(12) United States Patent
Caffrey et al.

(10) Patent No.: US 7,227,038 B2
(45) Date of Patent: Jun. 5, 2007

(54) ADAMANTANE DERIVATIVES, PROCESSES FOR THEIR PREPARATION AND PHARMACEUTICAL COMPOSITION CONTAINING THEM

(75) Inventors: Moya Caffrey, Loughborough (GB); Rhonan Ford, Loughborough (GB); Austen Pimm, Loughborough (GB)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/546,131

(22) PCT Filed: Feb. 19, 2004

(86) PCT No.: PCT/SE2004/000227

§ 371 (c)(1),
(2), (4) Date: Aug. 19, 2005

(87) PCT Pub. No.: WO2004/074224

PCT Pub. Date: Sep. 2, 2004

(65) Prior Publication Data
US 2006/0160904 A1 Jul. 20, 2006

(30) Foreign Application Priority Data
Feb. 21, 2003 (SE) .................................. 0300480

(51) Int. Cl.
*C07C 233/65* (2006.01)
*A61K 31/165* (2006.01)

(52) U.S. Cl. ........................ 564/165; 564/164; 514/620

(58) Field of Classification Search ................ 564/164, 564/165; 514/620
See application file for complete search history.

(56) References Cited

U.S. PATENT DOCUMENTS

| | | | |
|---|---|---|---|
| 3,464,998 A | 9/1969 | Krimmel | |
| 3,471,491 A | 10/1969 | Venkatachala et al. | |
| 4,349,552 A | 9/1982 | Takaya et al. | |
| 4,751,292 A | 6/1988 | Fox | |
| 6,201,024 B1 | 3/2001 | Baxter et al. | |
| 6,242,470 B1 | 6/2001 | Baxter et al. | |
| 6,492,355 B1 | 12/2002 | Alcaraz et al. | |
| 6,720,452 B2 * | 4/2004 | Alcaraz et al. | 564/165 |
| 6,949,539 B2 | 9/2005 | Alcaraz et al. | |
| 7,129,246 B2 | 10/2006 | Alcaraz et al. | |
| 2001/0003121 A1 | 6/2001 | Baxter et al. | |
| 2002/0193414 A1 | 12/2002 | Alcaraz et al. | |
| 2003/0013704 A1 | 1/2003 | Alcaraz et al. | |
| 2003/0144293 A1 | 7/2003 | Duplantter et al. | |
| 2004/0236109 A1 | 11/2004 | Van Straten et al. | |
| 2005/0090524 A1 | 4/2005 | Ford et al. | |
| 2006/0247257 A1 | 11/2006 | Dixon | |

FOREIGN PATENT DOCUMENTS

| BE | 650919 A | 7/1964 |
|---|---|---|
| DE | 1943404 A | 12/1970 |
| EP | 0002065 | 5/1979 |
| EP | 0867436 | 9/1998 |
| EP | 1310493 | 5/2003 |
| WO | WO 95/04720 | 2/1995 |
| WO | WO 99/18074 | 4/1999 |
| WO | WO 99/29660 | 6/1999 |
| WO | WO 99/29661 | 6/1999 |
| WO | WO 00/61569 | 10/2000 |
| WO | WO 01/42194 | 6/2001 |
| WO | WO 01/44170 | 6/2001 |
| WO | WO 02/096426 | 12/2002 |
| WO | WO 03/042191 | 5/2003 |
| WO | WO 03041707 | 5/2003 |
| WO | WO 03/080579 | 10/2003 |
| WO | WO 04/073704 | 9/2004 |
| WO | WO 04/105796 | 12/2004 |
| WO | WO 04/105797 | 12/2004 |

(Continued)

OTHER PUBLICATIONS

Accession No. 2003:42109, CAS Registry No. 487064-48-2, 2003.

(Continued)

*Primary Examiner*—Shailendra Kumar
(74) *Attorney, Agent, or Firm*—Fish & Richardson P.C.

(57) ABSTRACT

The invention provides compounds of formula

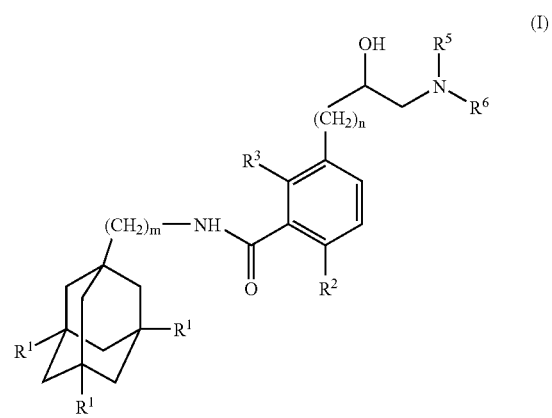

in which m, n, $R^1$, $R^2$, $R^3$, $R^4$, and $R^5$, have the meanings defined in the specification; processes for their preparation; pharmaceutical compositions containing them; a process for preparing the pharmaceutical compositions; and their use in therapy.

16 Claims, No Drawings

FOREIGN PATENT DOCUMENTS

| | | |
|---|---|---|
| WO | WO 04/105798 | 12/2004 |
| WO | WO 05/014529 | 2/2005 |
| WO | WO 05/025571 | 3/2005 |

OTHER PUBLICATIONS

Alcaraz et al., Preparation of Adamantane Derivatives as P2X7 Receptor Antagonists, CAS Accession No. 2001:904155.

Alcaraz et al., "Novel P2X7 Antagonists" *Bioorganic and Medicinal Chemistry Letters*, 13:4043-4046 (2003).

Baxter et al., "Hit-to-Lead Studies: The Discovery of Potent Adamantane Amide P2X7 Receptor Antagonists," *Bioorganic and Medical Chemistry Letters*, 13:4047-4050 (2003).

Bourrie et al., "SSR125329A, A High Affinity Receptor Ligand with Potent Anti-Inflammatory Properties," *Eur. J. of Pharm.*, 456:123-131 (2002).

Costakis et al., "Synthesis of Some Adamantane Derivatives of 2-Aminobenzothiazoles", *Journal of Medicinal Chemistry* 14(12):1222-1223 (1971).

Dell 'Antonio et al., "Antinociceptive effect of a new $P_{2z}P2X7$ antagonist, oxidized ATP, in arthritic rats", *Neuroscience Letters* 327:87-90 (2002).

Di Virgilio et al., "Purinergic P2X—Receptor: A Pivotal in Inflammation and Immunomodulation", *Drug Development Research* 45:207-213 (1998).

Ferrari et al., "Extracellular ATP Triggers IL-1 β Release by Activating the Purinergic P2Z Receptor of Human Macrophages", *J. Immunol.* 159:1451-1458 (1997).

Ferrari et al., "Purinergic Modulation of Interleukin- 1 β Release from Microglial Cells Stimulated with Barterial Endotoxin", *J. Exp. Med.* 185(3):579-582 (1997).

Henderson et al., "Inhibition of interleukin-1 -induced synovitis and articular cartilage proteoglycan loss in the rabbit knee by recombinant human interleukin-1 receptor antagonist", *Cytokine* 3(3):246-249 (1991).

Ho et al., "Synthesis of a Peptidomimetic Tricyclic Tetrahydrobenzo[*ij*] quinoline as a VLA-4 Antagonist", *Org. Chem.* 65:6743-6748, p. 6745, scheme 5, (27) (2000).

Humphreys et al., "Modulation of $P2X_7$ nucleotide receptor expression by pro-and anti-inflammatory stimuli in THP-1 monocytes", *Journal of Leukocyte Biology* 64:265-273 (1998).

Kadota et al., "Significance of IL-1 β and IL-1 receptor antagonist (IL-1 Ra) in bronchoalveolar lavage fluid (BALF) in patients with diffuse panbronchiolitis (DPB)", *Clin Exp. Immunol.* 103:461-466 (1996).

Kburana et al., "Clinical aspects of rheumatoid arthritis", Pathophysiology, vol. 12, Issue 3, Abstract (2005).

Kirkham, "Interleukin-1, Immune Activation Pathways, and Different Mechanisms in Osteoarthritis and Rheumatoid Arthritis", *Annals of the Rheumatic Diseases*, 50:395-400 (1991).

Li et al., "Should atherosclerosis be considered a cancer of the vascular wall?" *Medical Hypotheses*, 64:694-698 (2005).

Otterness et al., "Possible Role of IL-1 in Arthritis: Effects of Prostaglandins in the Regulation of IL-1 Synthesis and Actions", Agent Act 39 (Suppl):109-120 (1993).

Mackenzie et al., "Could rheumatoid arthritis have an infectious aetiology?" Drug Discovery Today: Disease Mechanism, vol. 2, Issue 3, Abstract (2005).

Rains et al., "Sulfasalazine, A review of its Pharmacoligical Properties and Therapeutic Efficacy in the Treatment of Rheumatoid Arthritis", *Drugs* 50:137-156 (1995).

Richards et al., "Substituted 2-Phenyl-benzimidazole Derivatives: Novel Compounds that Suppress Key Markers of Allergy," Eur. J. of Medic. Chem., 41:950-969 (2006).

Sakito et al., "Interleukin 1 β, Tumor Necrosis Factor Alpha, and Interleukin 8 in Bronchoalveolar Lavage Fluid of Patients with Diffuse Panbronchiolitis: A Potential Mechanism of Macrolide Therapy", *Respiration* 63:42-48 (1996).

Seventh International Symposium on Adenosine & Adenine Nucleotides: "Adenosin-und Purinrezeptoren als Targets neuer Arneimittel", *Deutsche Apotheker Zeitung* 142(36):62-65 (2002).

STN International, File REGISTRY, see RN 405068-97-5, 405070-41-9, 405076-22-4, Apr. 14, 2002.

STN International, File REGISTRY, see RN 445032-09-7, Aug. 30, 2002.

STN International, File CHEMCATS, Accession No. 2001:48444, May 14, 2001, NS18552, 2-Quinolinecarboxamide, N-(tricycle[3. 3.1.13,7]dec-1-ylmethyl), CAS Registry No. 313688-07-2.

STN International, File REGISTRY, see RN 401622-10-4, Mar. 24, 2002.

van den Berg, Lessons from animals models of osteoarthritis, *Curr. Opin. Rheumatol*, 13(5): 452-6 (2001)

Yu et al., "Inhibition on IL-1 Release from Human Monocytes and Suppression of Streptococcal Cell Wall and Adjuvant-induced Arthritis in Rats by an Extract of *Tripterygium wilfordii* Hook", *Gen. Pharmac.* 25(6):1115-1122 (1994).

\* cited by examiner

ADAMANTANE DERIVATIVES, PROCESSES FOR THEIR PREPARATION AND PHARMACEUTICAL COMPOSITION CONTAINING THEM

CROSS-REFERENCE TO RELATED APPLICATIONS

This application is the National Stage of International Application No. PCT/SE2004/000227, filed Feb. 19, 2004, which claims the benefit of Swedish Patent Application Serial No. 0300480-1, filed Feb. 21, 2003. The contents of both applications are hereby incorporated by reference in their entireties.

The present invention relates to adamantane derivatives, processes for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). $P2X_7$ receptors are also located on antigen-presenting cells (APC), keratinocytes, salivary acinar cells (parotid cells), hepatocytes and mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of formula

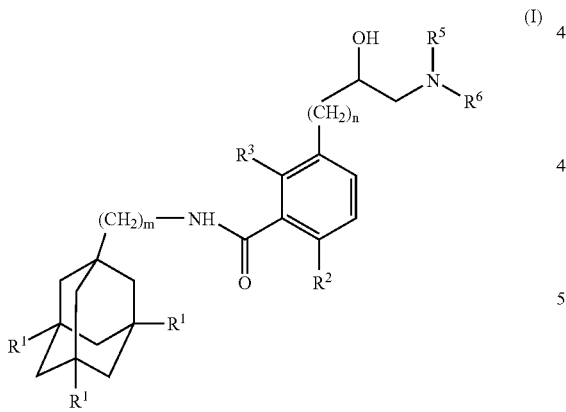

(I)

wherein m represents 1, 2 or 3, preferably 1 or 2;

each $R^1$ independently represents a hydrogen or halogen (e.g. fluorine, chlorine, bromine or iodine) atom, preferably a hydrogen atom;

one of $R^2$ and $R^3$ represents halogen, nitro, amino, hydroxyl, or a group selected from (i) $C_1$–$C_6$ alkyl optionally substituted by at least one halogen atom, (ii) $C_3$–$C_8$ cycloalkyl, (iii) $C_1$–$C_6$ alkoxy optionally substituted by at least one halogen atom, and (iv) $C_3$–$C_8$ cycloalkyloxy, and the other of $R^2$ and $R^3$ represents a hydrogen or halogen atom;

n represents 0, 1 or 2; and $R^4$ and $R^5$ each independently represent a hydrogen atom or a $C_1$–$C_6$ alkyl group optionally substituted by at least one substituent selected from hydroxyl, halogen and $C_1$–$C_6$ alkoxy;

or a pharmaceutically acceptable salt or solvate thereof.

In the context of the present specification, unless otherwise indicated, an alkyl substituent or alkyl moiety in a substituent group may be linear or branched. Examples of alkyl groups/moieties containing up to 6 carbon atoms include methyl, ethyl, n-propyl, isopropyl, n-butyl, isobutyl, tert-butyl, n-pentyl and n-hexyl. Further, it should be appreciated that if $R^4$ and/or $R^5$ represents a $C_1$–$C_6$ alkyl group substituted by at least one substituent being a hydroxyl or $C_1$–$C_6$ alkoxy group, the hydroxyl or alkoxy substituent will not be attached to the carbon atom which is adjacent to the nitrogen atom.

One of $R^2$ and $R^3$ represents a halogen (e.g. fluorine, chlorine, bromine or iodine), nitro, amino ($-NH_2$), hydroxyl, or a group selected from (i) $C_1$–$C_6$ alkyl, preferably $C_1$–$C_4$ alkyl, optionally substituted by at least one (e.g. one, two, three or four) halogen atom(s) as defined above, (ii) $C_3$–$C_8$ cycloalkyl (e.g. cyclopropyl, cyclobutyl, cyclopentyl or cyclohexyl), (iii) $C_1$–$C_6$ alkoxy, preferably $C_1$–$C_4$ alkoxy, optionally substituted by at least one (e.g. one, two, three or four) halogen atom(s) as defined above, and (iv) $C_3$–$C_8$ cycloalkyloxy (e.g. cyclopropyloxy, cyclobutyloxy, cyclopentyloxy or cyclohexyloxy), and the other of $R^2$ and $R^3$ represents a hydrogen or halogen atom as defined above.

In one embodiment of the invention, one of $R^2$ and $R^3$ represents a halogen (such as a chlorine or bromine) atom and the other of $R^2$ and $R^3$ represents a hydrogen atom.

In an embodiment of the invention, m is 1.

In another embodiment of the invention, $R^3$ represents a hydrogen atom.

In another embodiment of the invention, n is 1.

In a further embodiment of the invention, n is 1 and the compound of formula (I) has the following stereochemistry:

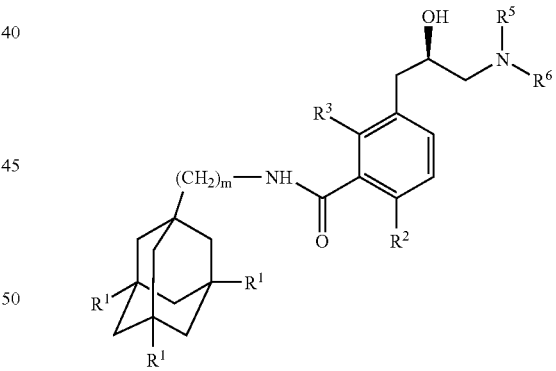

$R^4$ and $R^5$ each independently represent a hydrogen atom or a $C_1$–$C_6$, for example, $C_1$–$C_4$ or $C_1$–$C_3$, alkyl group which may be optionally substituted by at least one substituent (e.g. one, two, three or four substituents independently) selected from hydroxyl, halogen (e.g. fluorine, chlorine, bromine or iodine) and $C_1$–$C_6$, for example, $C_1$–$C_4$, alkoxy (e.g. methoxy, ethoxy, n-propoxy, n-butoxy, n-pentoxy and n-hexoxy.

In an embodiment of the invention, $R^4$ and $R^5$ each independently represent a hydrogen atom or a $C_1$–$C_6$ alkyl group which may be optionally substituted by at least one, e.g. one or two, hydroxyl group(s).

In another embodiment of the invention, $R^4$ and $R^5$ each independently represent a hydrogen atom or a group selected from $-CH_3$, $-C_2H_5$, $-CH(CH_3)_2$, $-CH_2OH$, $-(CH_2)_2$ OH, —(CH$_2$)$_3$OH, —CH(CH$_3$)CH$_2$OH, —CH$_2$CH(CH$_3$) OH, —CH$_2$CH(OH)CH$_3$, —CH$_2$CH(OH)CH$_2$OH, —CH$_2$C (CH$_3$)$_2$OH, —CH(isopropyl)CH$_2$OH, —CH(CH$_2$OH)$_2$, or —CH$_2$C(CH$_3$)$_2$CH$_2$OH.

In a further embodiment of the invention, R$^4$ and R$^5$ each independently represent a hydrogen atom or a group selected from —CH$_3$, —C$_2$H$_5$, —CH(CH$_3$)$_2$ and —(CH$_2$)$_3$OH.

In an embodiment of the invention, there is provided a subset of compounds of formula (I), and pharmaceutically acceptable salts and solvates thereof, in which:
m represents 1;
each R$^1$ represents a hydrogen atom;
one of R$^2$ and R$^3$ represents a halogen atom, and the other of R$^2$ and R$^3$ represents a hydrogen atom;
n is 0, 1 or 2; and
R$^4$ and R$^5$ each independently represent a hydrogen atom or a group selected from —CH$_3$, —C$_2$H$_5$, —CH(CH$_3$)$_2$ and, —(CH$_2$)$_3$OH.

In another embodiment of the invention, there is provided a further subset of compounds of formula (I), and pharmaceutically acceptable salts and solvates thereof, in which:
m represents 1;
each R$^1$ represents a hydrogen atom;
one of R$^2$ and R$^3$ represents a halogen atom, and the other of R$^2$ and R$^3$ represents a hydrogen atom;
n is 0, 1 or 2; and
one of R$^4$ and R$^5$ represents a hydrogen atom or —CH$_3$ and the other of R$^4$ and R$^5$ represents a group selected from —CH$_3$, —C$_2$H$_5$, —CH(CH$_3$)$_2$ and —(CH$_2$)$_3$OH.

Examples of compounds of the invention include:
2-Chloro-5-[(3S)-3-hydroxy-4-(methylamino)butyl]-N-(tricyclo[3.3.1.1$^{3,7}$]dec-1-ylmethyl)benzamide,
2-Chloro-5-[(3S)-3-hydroxy-4-(ethylamino)butyl]-N-(tricyclo[3.3.1.1$^{3,7}$]dec-1-ylmethyl)benzamide,
2-Chloro-5-[(3S)-3-hydroxy-4-(1-methylethylamino)butyl]-N-(tricyclo[3.3.1.1$^{3,7}$]dec-1-ylmethyl)benzamide,
2-Chloro-5-[(3R)-3-hydroxy-4-(methylamino)butyl]-N-(tricyclo[3.3.1.1$^{3,7}$]dec-1-ylmethyl)benzamide,
2-Chloro-5-[(2R)-3-(ethylamino)-2-hydroxypropyl]-N-(tricyclo[3.3.1.1$^{3,7}$]dec-1-ylmethyl)-benzamide hydrochloride,
2-Chloro-5-[(2R)-2-hydroxy-3-[(1-methylethyl)amino] propyl]-N-(tricyclo[3.3.1.13$^{3,7}$dec-1-ylmethyl)-benzamide hydrochloride,
2-Chloro-5-[(2R)-2-hydroxy-3-[(3-hydroxypropyl) amino]propyl]-N-(tricyclo[3.3.1.1$^{3,7}$]dec-1-ylmethyl)-benzamide hydrochloride,
2-Chloro-5-[(2R)-3-(dimethylamino)-2-hydroxypropyl]-N-(tricyclo[3.3.1.1$^{3,7}$]dec-1-ylmethyl)-benzamide hydrochloride,
2-Chloro-5-[(1S)-1-hydroxy-2-(methylamino)ethyl]-N-(tricyclo[3.3.1.1$^{3,7}$]dec-1-ylmethyl)benzamide hydrochloride,
2-Chloro-5-[(1R)-1-hydroxy-2-(methylamino)ethyl]-N-(tricyclo[3.3.1.1$^{3,7}$]dec-1-ylmethyl)benzamide hydrochloride,
2-Chloro-5-[(1R)-2-(ethylamino)-1-hydroxyethyl]-N-(tricyclo[3.3.1.1$^{3,7}$]dec-1-ylmethyl)benzamide,
2-Chloro-5-[(1R)-1-hydroxy-2-[(3-hydroxypropyl) amino]ethyl]-N-(tricyclo[3.3.1.1$^{3,7}$]dec-1-ylmethyl) benzamide,
2-Chloro-5-[(2S)-2-hydroxy-3-(methylamino)propyl]-N-(tricyclo[3.3.1.1$^{3,7}$]dec-1-ylmethyl)-benzamide hydrochloride,
2-Chloro-5-[(2S)-3-(ethylamino)-2-hydroxypropyl]-N-(tricyclo[3.3.1.1$^{3,7}$]dec-1-ylmethyl)-benzamide hydrochloride,
2-Chloro-5-[(2R)-2-hydroxy-3-(methylamino)propyl]-N-(tricyclo[3.3.1.1$^{3,7}$]dec-1-ylmethyl)benzamide benzoic acid salt, and all pharmaceutically acceptable salts and solvates of any one thereof.

The present invention further provides a process for the preparation of a compound of formula (I) as defined above, or a pharmaceutically acceptable salt or solvate thereof, which comprises:
(i) when n is 0, reacting a compound of formula

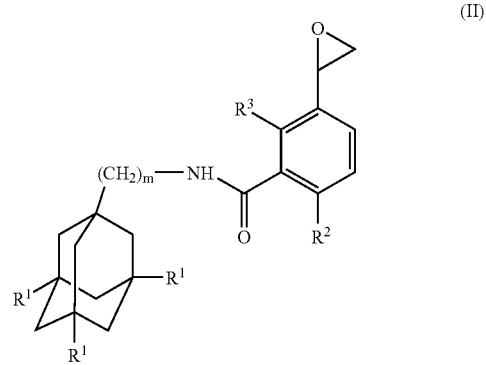

(II)

wherein m, R$^1$, R$^2$ and R$^3$ are as defined in formula (I), with a compound of formula (III), HNR$^4$R$^5$, wherein R$^4$ and R$^5$ are as defined in formula (I); or
(ii) when n is 1, reacting a compound of formula

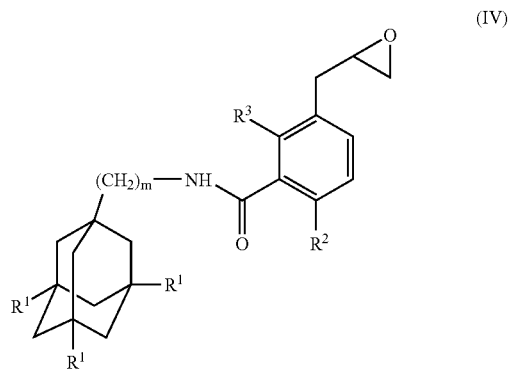

(IV)

wherein m, R$^1$, R$^2$ and R$^3$ are as defined in formula (I), with a compound of formula (III) as defined in (i) above; or
(iii) when n is 2, reacting a compound of formula

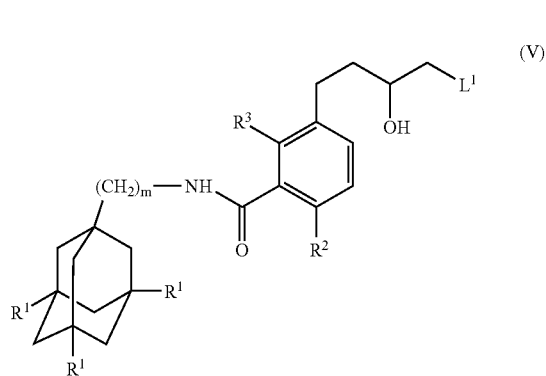

(V)

wherein L$^1$ is a leaving group (e.g. halogen, nitrobenzenesulfonyl, methanesulfonyl or an alternative leaving group for nucleophilic displacement reactions) and m, $R^1$, $R^2$ and $R^3$ are as defined in formula (I), with a compound of formula (III) as defined in (i) above; or (iv) when n is 1, reacting a compound of formula

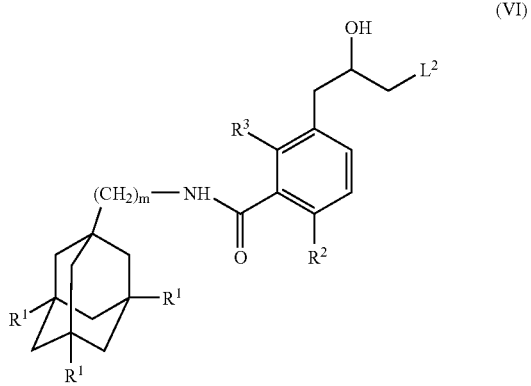

(VI)

wherein $L^2$ is a leaving group (e.g. halogen, nitrobenzenesulfonyl, methanesulfonyl or an alternative leaving group for nucleophilic displacement reactions) and m, $R^1$, $R^2$ and $R^3$ are as defined in formula (I), with a compound of formula (III) as defined in (i) above;

and optionally after (i), (ii) (iii) or (iv) carrying out one or more of the following:
converting the compound obtained to a further compound of formula (I)
forming a pharmaceutically acceptable salt or solvate of the compound.

In process (i), the compound of formula (II) may be conveniently synthesised by reacting a compound of formula

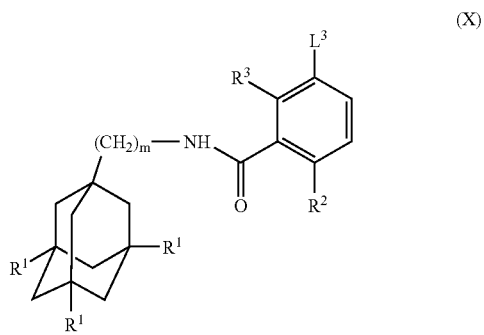

(X)

wherein $L^3$ represents a leaving group (e.g. halogen, phosphate, trifluoromethane sulphonate or an alternative leaving group for metal catalysed coupling reactions) and m, $R^1$, $R^2$ and $R^3$ are as defined in formula (I), with a compound of formula

(XI)

wherein $L^4$ represents a leaving group (e.g. trialkyltin, boronic acid or an alternative leaving group for metal catalysed coupling reactions) under metal catalysed coupling conditions such as tetrakis(triphenylphosphine)palladium(0).

The subsequent oxidation reaction may be performed with a reagent such as m-chloroperbenzoic acid in a suitable solvent such as dichloromethane.

Compounds of formula (II) may also be prepared by reacting a compound of formula

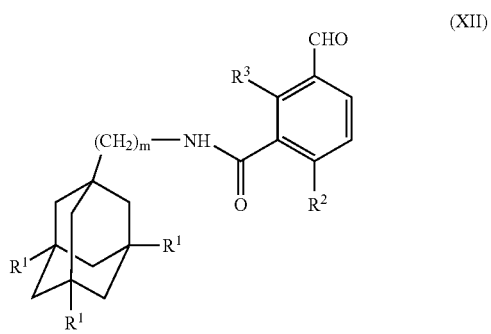

(XII)

wherein m, $R^1$, $R^2$ and $R^3$ are as defined in formula (I), with a compound of formula (XIII) or (XIV) suitably deprotonated by a base such as sodium hydride,

(XIII)

(XIV)

Reaction of the resultant epoxide may be performed by addition of the required amine of formula (III) at room temperature or at elevated temperature. An example of a compound of formula (XIII) is trimetlylsulfonium iodide.

In process (ii), the compound of formula (IV) may be conveniently synthesised by reacting a compound of formula

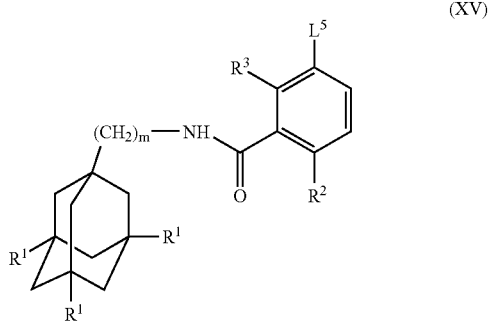

(XV)

wherein $L^5$ represents a leaving group (e.g. halogen, phosphate, trifluoromethane sulphonate or an alternative leaving group for metal catalysed coupling reactions) and m, $R^1$, $R^2$ and $R^3$ are as defined in formula (I), with a compound of formula

(XVI)

wherein $L^6$ represents a leaving group (e.g. trialkyltin, trialkylsilane, boronate, boronic acid or an alternative leaving group for metal catalysed coupling reactions) under metal catalysed coupling conditions such as dichlorobis(triphenylphosphine)palladium(II). The subsequent oxidation reaction may be performed with a reagent such as m-chloroperbenzoic acid or a combination of pyrazole, methyltrioxorhenium(VII) and hydrogen peroxide in a suitable solvent such as dichloromethane.

Compounds of formula (IV) may also be prepared by reacting a compound of formula

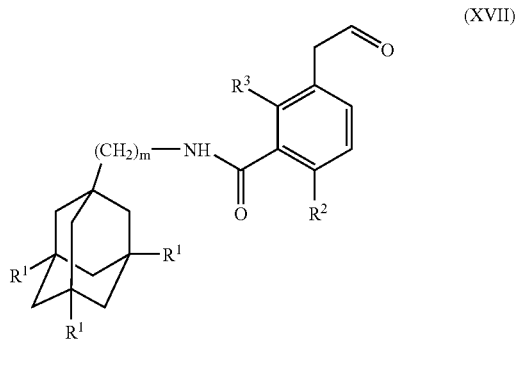

(XVII)

wherein m, $R^1$, $R^2$ and $R^3$ are as defined in formula (I), with a compound of formula (XIII) or (XIV) as defined above suitably deprotonated by a base such as sodium hydride.

Reaction of the resultant epoxide may be performed by addition of the required amine of formula (III) at room temperature or at elevated temperature.

In process (iii), the compound of formula (V) may be conveniently synthesised by reacting a compound of formula

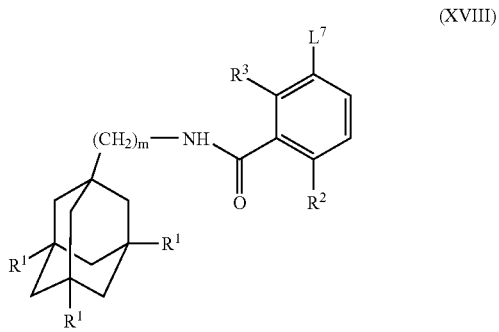

(XVIII)

wherein $L^7$ represents a leaving group (e.g. halogen, phosphate, trifluoromethane sulphonate or an alternative leaving group for metal catalysed coupling reactions) and m, $R^1$, $R^2$ and $R^3$ are as defined in formula (I), with a compound of formula

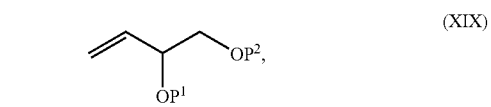

(XIX)

wherein $P^1$ and $P^2$ each independently represent a protecting group, in the presence of tetrakis(triphenylphosphine)palladium(0), followed by removal of the protecting groups with a reagent such as hydrochloric acid and reaction with a reagent such as methanesulphonyl chloride. Protecting groups $P^1$ and $P^2$ may be selected from any of the wide range of hydroxyl protecting groups known in the art.

The compound of formula (V) may be reacted with the amine of formula (III) at room temperature or at elevated temperature.

In process (iv), the compound of formula (VI) may be conveniently synthesised by reacting a compound of formula

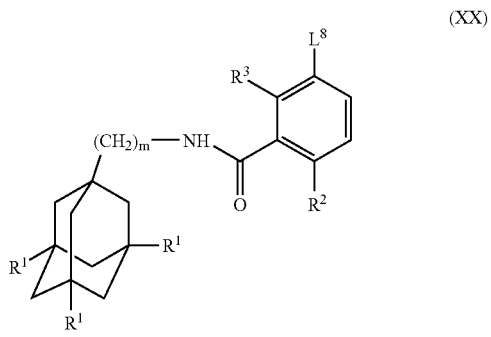

(XX)

wherein $L^8$ represents a leaving group (e.g. halogen, phosphate, trifluoromethane sulphonate or an alternative leaving group for metal catalysed coupling reactions) and m, $R^1$, $R^2$ and $R^3$ are as defined in formula (I) (suitably metallated with a reagent such as butyllithium or isopropylmagnesium chloride followed by addition of copper(I) bromide dimethylsulphide complex), with a compound of formula

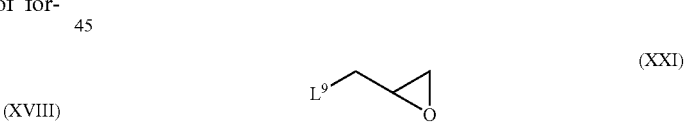

(XXI)

wherein $L^9$ is a leaving group (e.g. halogen, nitrobenzenesulfonyl, methanesulfonyl or an alternative leaving group for nucleophilic displacement reactions), followed by reaction with a reagent such as methanesulphonyl chloride.

The compound of formula (VI) may be reacted with the amine of formula (III) at room temperature or at elevated temperature.

Compounds of formula (I) can be converted into further compounds of formula (I) using standard procedures. For example, compounds of formula (I) in which one of $R^2$ and $R^3$ represents a halogen atom may be converted to a corresponding compound of formula (I) in which one of $R^2$ and $R^3$ represents a $C_1$–$C_6$ alkyl group by reaction with an alkyl Grignard reagent (e.g. methyl magnesium bromide) in the presence of a catalyst such as [1,3-bis(diphenylphosphino)propane]dichloronickel (II) in a solvent such as tetrahydrofuran.

Compounds of formula (X), (XII), (XV), (XVII), (XVIII) referred to above may be prepared by known chemistry, for example by methods according or analogous to those described in WO 99/29661 and WO 00/61569.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention. Enantiomerically pure forms are particularly desired.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, inflammatory bowel disease, Crohn's disease, ulcerative colitis, atherosclerosis, growth and metastases of malignant cells, myoblastic leukaemia, diabetes, Alzheimer's disease, meningitis, osteoporosis, bum injury, ischaemic heart disease, stroke, varicose veins, sarcoidosis, rhinitis, acute and chronic pain, multiple sclerosis, myeloma, bone loss associated with malignancy and inflammatory and neurodegenerative diseases of the eye such as scleritis, episcleritis, uveitis, Sjogrens syndrome-keratoconjuctivitis, sclerokeratitis, optic neuritis, diabetic retinopathy, retinitis pigmentosa, antimalarial—induced retinopathy.

Accordingly, the present invention provides a compound of formula (I) or a pharmaceutically acceptable salt or solvate thereof as hereinbefore defined for use in therapy.

In another aspect, the invention provides the use of a compound of formula (I) or a pharmaceutically acceptable salt or solvate thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, osteoarthritis, inflammatory bowel disease, atherosclerosis or psoriasis) which comprises administering a therapeutically effective amount of a compound of formula (I) or a pharmaceutically acceptable salt or solvate thereof as hereinbefore defined to a patient.

The invention also provides a method of treating an obstructive airways disease (e.g. asthma or COPD) which comprises administering to a patient a therapeutically effective amount of a compound of formula (I) or a pharmaceutically acceptable salt or solvate thereof as hereinbefore defined to a patient.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I) or a pharmaceutically acceptable salt or solvate thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt or solvate thereof as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention further relates to combination therapies for the treatment of any one of rheumatoid arthritis, osteoarthritis, osteoporosis, psoriasis, inflammatory bowel diseases, COPD, asthma, allergic rhinitis or cancer or the neurodegenerative diseases such as multiple sclerosis, Alzheimer's disease or stroke. For the treatment of rheumatoid arthritis, the compounds of the invention may be combined with "biological agents" such as TNF-α inhibitors such as anti-TNF monoclonal antibodies (such as Remicade, CDP-870 and Humira) and TNF receptor immunoglobulin molecules (such as Enbrel.reg.). IL-1 receptor antagonist (such as Anakinra) and IL-1 trap, IL-18 receptor, anti-IL-6 Ab, anti-CD20 Ab, anti-IL-15 Ab and CTLA4Ig.

Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin. The COX-2 inhibitors (such as meloxicam, celecoxib, rofecoxib, valdecoxib and etoricoxib) and the cylco-oxygenase inhibiting nitric oxide donors (CINOD's) and the "disease modifying agents" (DMARDs) such as methotrexate, sulphasalazine, cyclosporine A, leflunomide; ciclesonide; hydroxychloroquine, d-penicillamine, auranofin or parenteral or oral gold.

The present invention still her relates to the combination of a compound of the invention together with a leukotriene biosynthesis inhibitor, 5-lipoxygenase (5-LO) inhibitor or 5-lipoxygenase activating protein (FLAP) antagonist selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2n cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonists for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic $H_1$ receptor antagonists including cetirizine, loratadine, desloratadine, fexofenadine, asterizole, azelastine, and chlorpheniramine.

The present invention still further relates to the combination of a compound of the invention together with a gastroprotective $H_2$ receptor antagonist or the proton pump inhibitors (such as omeprazole)

The present invention still further relates to the combination of a compound of the invention together with an $\alpha_1$- and $\alpha_2$-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethyl-norepinephrine hydrochloride.

The present invention still further relates to the combination of a compound of the invention together with anti-cholinergic agents including ipratropium bromide; tiotropium bromide; oxitropium bromide; pirenzepine; and telenzepine.

The present invention still further relates to the combination of a compound of the invention together with $\beta_1$- to $\beta_4$-adrenoceptor agonists including metaproterenol isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C-C family); CXCR1, CXCR3, CXCR4 and CXCR5 (for the C-X-C family) and $CX_3CR1$ for the $C-X_3-C$ family.

The present invention still further relates to the combination of a compound of the invention together with an insulin-like growth factor type I (IGF-1) mimetic.

The present invention still further relates to the combination of compound of the invention together with an inhaled glucocorticoid with reduced systemic side effects, including prednisone, prednisolone, flunisolide, triamcinolone acetonide, beclomethasone dipropionate, budesonide, fluticasone propionate, and mometasone furoate.

The present invention still further relates to the combination of a compound of the invention together with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; (j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFβ); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists selected from the group consisting of NKP-608C; SB-233412 (talnetant); and D-4418; and (t) elastase inhibitors selected from the group consisting of UT-77 and ZD-0892 (u) induced nitric oxide synthase inhibitors (iNOS) or (v) chemoattractant receptor-homologous molecule expressed on TH2 cells, (CRTH2 antagonists).

The present invention still further relates to the combination of a compound of the is invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, induced nitric oxide synthase inhibitors (iNOS inhibitors), COX-2 inhibitors such as celecoxib, valdecoxib, rofecoxib and etoricoxib, and the cylco-oxygenase inhibiting nitric oxide donors (CI-NOD's) analgesics (such as paracetamol and tramadol), cartilage sparing agents such as diacerein, doxycyline and glucosamine, and intra-articular therapies such as corticosteroids and hyaluronic acids such as hyalgan and synvisc.

The compounds of the invention can also be used in combination with existing therapeutic agents for the treatment of inflammatory bowel diseases (Ulcerative colitis and Crohn's disease). Suitable agents to be used include sulphasalazine, 5-amino-salicylates, the thiopurines, azathioprine and 6-mecaptorurine and corticosteroids such as budesonide.

The compounds of the present invention may also be used in combination with anticancer agents such as endostatin and angiostatin or cytotoxic drugs such as adriamycin, daunomycin, cis-platinum, etoposide, taxol, taxotere and farnesyl transferase inhibitors, VegF inhibitors, COX-2 inhibitors and antimetabolites such as methotrexate, antineoplastic agents, especially antimitotic drugs including the vinca alkaloids such as vinblastine and vincristine.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comp inhibitors such as Tasmar, A-2 inhibitors, dopamine reuptake inhibitors, NMDA antagonists, Nicotine agonists, Dopamine agonists and inhibitors of neuronal nitric oxide synthase), and anti Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The present invention will now be further explained by reference to the following illustrative examples. In the examples the NMR spectra were measured on a Varian Unity spectrometer at a proton frequency of either 300 or 400 MHz. The MS spectra were measured on either a Agilent 1100 MSD G1946D spectrometer or a Hewlett Packard HP1100 MSD G1946A spectrometer. Preparative HPLC separations were performed using a Waters' Symmetry™ or Xterra™ column or a Novapak™ column.

EXAMPLE 1

2-Chloro-5-[(3S)-3-hydroxy-4-(methylamino)butyl]-N-(tricyclo[3.3.1.1$^{3,7}$]dec-1-ylmethyl)benzamide, hydrochloride

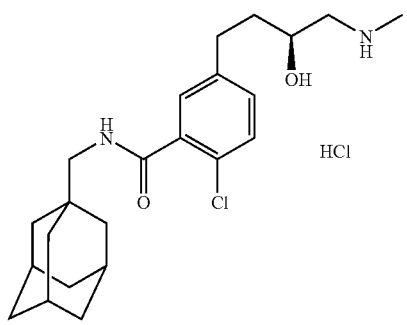

a) 5-Ethenyl-2,2,3,3,8,8,9,9-octamethyl-(5S) 4,7-dioxa-3,8-disiladecane

Imidazole (4 g) was added portionwise to a solution of (2S)-3-butene-1,2-diol (2 g) and chloro(1,1-dimethylethyl) dimethyl-silane (7 g) in N,N-dimethylformamide (20 mL).

The mixture was stirred at room temperature for 24 hours. The biphasic reaction mixture was poured into ether and washed with water (×3) and brine, dried over anhydrous magnesium sulfate, filtered and evaporated, to give an oil (7.5 g). Purification by bulb-bulb distillation (130–150° C. at 3 mm Hg), gave the sub-titled compound as an oil (5.3 g).

$^1$H NMR (300 MHz, CDCl$_3$) δ 5.92–5.81 (1H, m), 5.26 (1H, d), 5.11 (1H, d), 4.16 (1H, q), 3.57–3.42 (2H, m), 0.90 (18H, s), 0.05 (12 H,s).

b) 2-Chloro-5-[(3S)-3,4-dihydroxybutyl]-N-(tricyclo[3.3.1.1$^{3,7}$]dec-1-ylmethyl)benzamide 9-Borabicyclo[3.3.1]nonane dimer (1.8 g) was added at room temperature to a solution of 5-ethenyl-2,2,3,3,8,8,9,9-octamethyl-(5S) 4,7-dioxa-3,8-disiladecane (Example 1 a) (1.0 g) in tetrahydrofuran (20 mL), under nitrogen. N,N-dimethylformamide (20 mL) was added to the reaction mixture and degassed by bubbling nitrogen through the reaction mixture for 30 minutes. A solution of 2-chloro-5-iodo-N-(tricyclo[3.3.1.1$^{3,7}$]dec-1-ylmethyl)benzamide (1.3 g) (prepared as described in WO99/29661) in N,N-dimethylformamide (10 mL) was added to the reaction mixture and degassing continued for 45 min. Potassium carbonate (1.0 g) and tetrakis(triphenylphosphine)palladium(0) (0.2 g) were added to the reaction mixture and heated to 80–90° C. for 24 hours under nitrogen. On cooling to room temperature the reaction mixture was poured into ethyl acetate and the organic layer washed with water, aqueous hydrochloric acid (2M), brine, dried over anhydrous magnesium sulfate, filtered and evaporated. The resulting oil was redissolved in dichloromethane (50 mL) and hydrochloric acid in 1,4-dioxane (4M, 5 mL) was added. After 18 hours the reaction mixture was concentrated and purified by column chromatography (gradient 0–5% methanol in dichloromethane). Further purification by reverse phase HPLC (gradient 25–95% acetonitrile (MeCN) in 0.2% aqueous ammonium acetate (NH$_4$AcO) on Symmetry™ column) gave the sub-titled product as a white solid (0.36 g).

$^1$H NMR (300 MHz, CDCl$_3$) δ 7.57 (1H, d), 7.31 (1H, d), 7.20 (1H, dd), 6.30 (1H, s), 3.76–3.56 (2H, m), 3.46 (1H, t), 3.18 (2H, d), 2.87–2.66 (2H, m), 2.34 (1H, s), 2.07–1.91 (4H, m), 1.80–1.54 (14H, m).

MS (APCI+) ion [M+H]$^+$ 392/4 m.p. 145–147° C.

$[α]_D^{25}$ (C=0.16 in MeOH) −16.4° c) 2-Chloro-5-[(3S)-3-hydroxy4-[(methylsulfonyl)oxy]butyl]-N-(tricyclo[3.3.1.1$^{3,7}$]dec-1-ylmethyl)benzamide Methanesulfonylchloride (0.08 mL) was added to a solution of 2-chloro-5-[(3S)-3,4-dihydroxybutyl]-N-(tricyclo (3.3.1.1$^{3,7}$]dec-1-ylmethyl)benzamide (Example 1b) (0.33 g) and triethylamine (0.33 ml) in dichloromethane (10 mL). After 1 hour the reaction mixture was concentrated, redissolved in ethyl acetate and the organic layer washed with water, brine, dried over anhydrous magnesium sulfate, filtered and evaporated. Purification by normal phase HPLC (gradient 0–5% ethanol (EtOH) in dichloromethane on silica Novapak™ column), gave the sub-titled compound (0.14 g).

$^1$H NMR (300 MHz, CDCl$_3$) δ 7.57 (1H, d), 7.33 (1H, d), 7.20 (1H, dd), 6.31 (1H, s), 4.25–4.09 (2H, m), 3.96–3.81 (1H, m), 3.18 (2H, d), 3.06 (3H, s), 2.93–2.65 (2H, m), 2.30 (1H, d), 2.01 (3H, s), 1.87–1.57 (14H, m).

MS (APCI+) ion [M+H]$^+$ 470/2 d) 2-Chloro-5-[(3S)-3-hydroxy-4-(methylamino) butyl]-N-(tricyclo[3.3.1.1³,⁷]dec-1-ylmethyl)benzamide Aqueous methylamine (40%) (3 mL) was added to a solution of 2-chloro-5-[(3S)-3-hydroxy-4-[(methylsulfonyl)oxy]butyl]-N-(tricyclo[3.3.1.1³,⁷dec-1-ylmethyl)benzamide (Example 1c) (0.13 g) in acetonitrile (20 mL) and heated at 50° C. for 4 hours. Further aqueous methylamine (40%) (2 mL) was added and heating at 50° C. continued for a further 1 hour. On cooling the reaction mixture was concentrated and purified by solid phase extraction on Waters' SCX resin, eluting with ammonia in methanol (7M). The residue was dissolved in methanol (5 mL) and hydrochloric acid in dioxane (4M, 1 mL) was added, evaporation gave the titled compound (0.12 g).

$^1$H NMR (300 MHz, $d_6$-DMSO) δ 8.69–8.37 (2H, m), 8.29 (1H, t), 7.39 (1H, d), 7.31–7.22 (2H, m), 5.60–5.21 (1H, m), 3.81–3.65 (1H, m), 3.07–2.88 (3H, m), 2.88–2.57 (3H, m), 2.54 (3H, s), 1.95 (3H, s), 1.75–1.55 (8H, m), 1.52 (6H, s).

MS (APCI+) ion [M+H]$^+$ 405/7 m.p.>200° C. dec $[\alpha]_D^{21}$ (C=0.15 in MeOH) −2.4°

EXAMPLE 2

2-Chloro-5-[(3S)-3-hydroxy-4-(ethylamino)butyl]-N-(tricyclo[3.3.1.1³,⁷]dec-1-ylmethyl)benzamide, hydrochloride

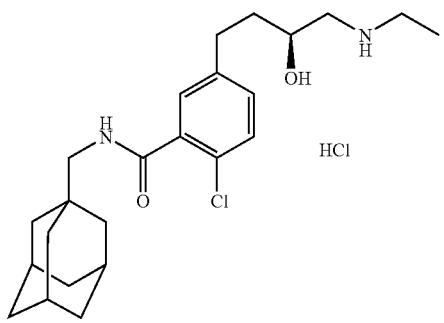

Aqueous ethylamine (70%) (2 mL) was added to a solution of 2-chloro-5-[(3S)-3-hydroxy-4-[(methylsulfonyl)oxy]butyl]-N-(tricyclo[3.3.1.1³,⁷]dec-1-ylmethyl)benzamide (Example 1c) (0.2 g) in acetonitrile (5 mL) and heated at 50° C. for 2.5 hours. On cooling the reaction mixture was concentrated and purified by solid phase extraction on Waters' SCX resin, eluting with ammonia in methanol (7M). Further purification by reverse phase HPLC (gradient 25–95% acetonitrile in 0.2% aqueous trifluoroacetic acid (TFA) on Symmetry™ column). The residue was dissolved in methanol (5 mL) and hydrochloric acid in 1,4-dioxane (4M, 1 mL) was added, evaporation and recrystallisation from acetonitrile, gave the titled compound (0.13 g).

$^1$H NMR (300 MHz, $d_6$-DMSO) δ 8.74–8.32 (2H, m), 8.30 (1H, t), 7.39 (1H, d), 7.33–7.21 (2H, m), 5.46 (1H, d), 3.84–3.68 (1H, m), 3.05–2.85 (5H, m), 2.85–2.55 (3H, m), 1.94 (3H, s), 1.79–1.55 (8H, m), 1.52 (6H, s), 1.19 (3H, t).

MS (APCI+) ion [M+H]$^+$ 419/421

EXAMPLE 3

2-Chloro-5-[(3S)-3-hydroxy-4-(1-methylethylamino)butyl]-N-(tricyclo[3.3.1.1³,⁷]dec-1-ylmethyl)benzamide, hydrochloride

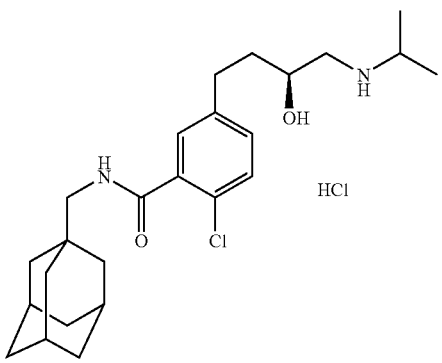

1-Methylethylamine (3 mL) was added to a solution of 2-chloro-5-[(3S)-3-hydroxy-4-[(methylsulfonyl)oxy]butyl]-N-(tricyclo[3.3.1.1³,⁷]dec-1-ylmethyl)benzamide (Example 1c) (0.22 g) in acetonitrile (10 mL) and heated at 50° C. for 18 hours. On cooling the reaction mixture was concentrated and purified by solid phase extraction on Waters' SCX resin, eluting with ammonia in methanol (7M). Further purification by reverse phase HPLC (gradient 25–95% acetonitrile in 0.2% aqueous trifluoroacetic acid on Symmetry™ column). The residue was dissolved in methanol (5 mL) and hydrochloric acid in dioxane (4M, 1 mL) was added, evaporation and recrystallisation from MeCN, gave the titled compound as the hydrochloric acid salt (30 mg).

$^1$H NMR (300 MHz, $d_6$-DMSO) δ 8.70–8.21 (3H, m), 7.40 (1H, d), 7.30–7.25 (2H, m), 5.44 (1H, d), 3.83–3.67 (1H, m), 3.38–3.19 (1H, m), 3.05–2.86 (3H, m), 2.87–2.55 (3H, m), 1.93 (3H, s), 1.77–1.47 (14H, m), 1.24 (3H, d), 1.22 (3H, d).

MS (APCI+) ion [M+H]$^+$ 433/435

EXAMPLE 4

2-Chloro-5-[(3R)-3-hydroxy4-(methylamino)butyl]-N-tricyclo[3.3.1.1³,⁷]dec-1-ylmethyl)benzamide

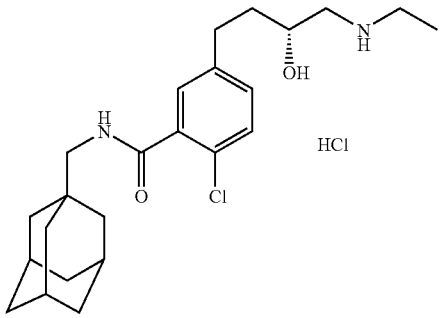

a) 5-Ethenyl-2,2,3,3,8,8,9,9-octamethyl-(5R) 4,7-dioxa-3,8-disiladecane

The sub-titled compound was prepared by the method of Example 1(a) using (2R)-3-butene-1,2-diol.

$^1$H NMR (300 MHz, CDCl$_3$) δ 5.92–5.81 (1H, m), 5.26 (1H, d), 5.11 (1H, d), 4.16 (1H, q), 3.57–3.42 (2H, m), 0.90 (18H, s), 0.05 (12H, s).

b) 2-Chloro-5-[(3R)-3,4-dihydroxybutyl]-N-(tricyclo[3.3.1.1$^{3,7}$]dec-1-ylmethyl)benzamide The sub-titled compound was prepared by the method of Example 1(b) using 5-ethenyl-2,2,3,3,8,8,9,9-octamethyl-(5R) 4,7-dioxa-3,8-disiladecane (product of Example 4a).

$^1$H NMR (300 MHz, CDCl$_3$) δ 7.57 (1H, d), 7.31 (1H, d), 7.20 (1H, dd), 6.30 (1H, s), 3.76–3.56 (2H, m), 3.46 (1H, t), 3.18 (2H, d), 2.87–2.66 (2H, m), 2.44 (1H, s), 2.07 (1H, s), 2.01 (3H, s), 1.80–1.54 (14H, m).

MS (APCI+) ion [M+H]$^+$ 392/4

$[α]_D^{24}$ (C=0.26 in MeOH)+14.0° c) 2-Chloro-5-[(3R)-3-hydroxy-4-[(methylsulfonyl)oxy]butyl]-N-(tricyclo [3.3.1.1$^{3,7}$]dec-1-ylmethyl)benzamide The sub-titled compound was prepared by the method of Example 1(c) using 2-chloro-5-[(3R)-3,4-dihydroxybutyl]-N-(tricyclo[3.3.1.1$^{3,7}$]dec-1-ylmethyl)benzamide.

$^1$H NMR (300 MHz, CDCl$_3$) δ 7.57 (1H, d), 7.33 (1H, d), 7.20 (1H, dd), 6.31 (1H, s), 4.25–4.09 (2H, m), 3.96–3.81 (1H, m), 3.18 (2H, d), 3.06 (3H, s), 2.93–2.65 (2H, m), 2.40 (1H, s), 2.01 (3H, s), 1.87–1.57 (14H, m).

MS (APCI+) ion [M+H]$^+$ 470/2 d) 2-Chloro-5-[(3R)-3-hydroxy-4-(methylamino)butyl]-N-(tricyclo[3.3.1.1$^{3,7}$]dec-1-ylmethyl)benzamide The titled compound was prepared by the method of Example 1(d) using 2-chloro-5-[(3R)-3-hydroxy-4-[(methylsulfonyl)oxy]butyl]-N-(tricyclo[3.3.1.1$^{3,7}$]dec-1-ylmethyl)benzamide.

$^1$H NMR (300 MHz, DMSO) δ 8.69–8.37 (2H, m), 8.29 (1H, t), 7.39 (1H, d), 7.31–7.22 (2H, m), 5.60–5.21 (1H, m), 3.81–3.65 (1H, m), 3.07–2.88 (3H, m), 2.88–2.57 (3H, m), 2.54 (3H, s), 1.95 (3H, s), 1.75–1.55 (8H, m), 1.52 (6H, s).

MS (APCI+) ion [M+H]$^+$ 405/7

EXAMPLE 5

2-Chloro-5-[(2R)-3-(ethylamino)-2-hydroxypropyl]-N-(tricyclo[3.3.1.1$^{3,7}$]dec-1-ylmethyl)-benzamide, hydrochloride

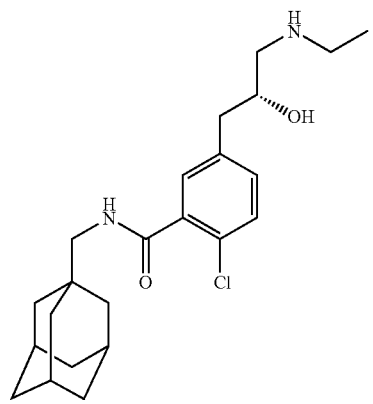

a) 2-Chloro-5-(2-propenyl)-N-(tricyclo[3.3.1.1$^{3,7}$]dec-1-ylmethyl)-benzamide 2-Chloro-5-iodo-N-(tricyclo[3.3.1.1$^{3,7}$]dec-1-ylmethyl)-benzamide (prepared as described in WO 99/29661) (7.74 g), tri-n-butylallyltin (5.99 g), dichlorobis(triphenylphosphine)palladium(II) (1.24 g), triphenylphosphine (1.86 g), lithium chloride (6.11 g) and N,N-dimethylformamide. (260 mL) were heated together under nitrogen from 110° C. to 130° C. over 20 minutes, and then at 130° C. for 25 minutes. The mixture was then cooled, poured into brine (500 mL), extracted into ethyl acetate (3×250 mL), dried over anhydrous magnesium sulfate, filtered and concentrated to give an oil. The crude mixture was purified by column chromatography eluting with 9:1 isohexane/ethyl acetate to give the sub-titled compound (5.23 g).

$^1$H NMR (300 MHz, CDCl$_3$) δ 7.54 (1H, s), 7.33–7.31 (1H, d), 7.20–7.16 (1H, d), 6.25 (1H, br s), 5.99–5.85 (1H, m), 5.13–5.06 (2H, m), 3.39–3.37 (2H, d), 3.19–3.17 (2H, d), 2.01 (3H, br s), 1.76–1.63 (6H, br AB), 1.58 (6H, br s).

MS (ES+) ion [M+H]$^+$ 344, 346 b) 2-Chloro-5-(oxiranylmethyl)-N-(tricyclo-[3.3.1.1$^{3,7}$]dec-1-ylmethyl)-benzamide 2-Chloro-5-(2-propenyl)-N-(tricyclo[3.3.1.1$^{3,7}$]dec-1-ylmethyl)-benzamide (Example 5a) (9.4 g), pyrazole (0.45 g) and methyltrioxorhenium(VII) (0.40 g) were stirred together in dichloromethane (40 mL) under nitrogen, and hydrogen peroxide (27.5% wt. solution in water, 13 mL) was added dropwise. The reaction was then monitored by HPLC/MS and further portions of pyrazole, methyltrioxorhenium(VII) and hydrogen peroxide were added over a period of 2 days until the reaction mixture consisted of a 1:1 mixture of starting material and product. The mixture was then poured into water (500 mL), extracted into dichloromethane (3×300 mL), washed with 2M aqueous hydrochloric acid (300 mL), brine (300 mL), saturated aqueous sodium thiosulfate (300 mL), dried over anhydrous magnesium sulfate, filtered and concentrated to give an oil. This was purified by column chromatography eluting with 2:1 isohexane/ethyl acetate to give the sub-titled compound (4.71 g).

$^1$H NMR (300 MHz, CDCl$_3$) δ 7.60 (1H, d), 7.38–7.34 (1H, d), 7.28–7.25 (1H, dd), 6.28 (1H, br t), 3.22–3.18 (2H, d), 3.17–3.11 (1H, m), 2.86–2.79 (3H, m), 2.53–2.52 (1H, m), 2.01 (3H, br s), 1.75–1.64 (6H, br AB), 1.59 (6H, br s).

MS (ES+) ion [M+H]$^+$ 360, 362 c) 2-Chloro-5-[(2R)-2-oxiranylmethyl]-N-(tricyclo [3.3.1.1$^{3,7}$]dec-1-ylmethyl)-benzamide (1R, 2R)-(−)-N,N'-Bis(3,5-di-t-butylsalicydene)-1,2-cyclohexanediaminocobalt(II) (0.30 g), acetic acid (0.15 mL) and toluene (3 mL) were stirred together in air for 1.25 hours. The solvents were then removed in vacuo and the resultant brown glass was dried under high vaccum for 2 hours. 2-Chloro-5-(oxiranylmethyl)-N-(tricyclo[3.3.1.1$^{3,7}$]dec-1-ylmethyl)-benzamide (Example 5b) (1.14 g), water (1.5 mL) and tetrahydrofuran (100 mL) were then added to this and the mixture stirred under nitrogen for 82 hours, concentrated and purified by column chromatography eluting with 2:1 isohexane/ethyl acetate to give the sub-titled compound (0.28 g).

MS (ES+) ion [M+H]$^+$ 360, 362 d) 2-Chloro-5-[(2R)-3-(ethylamino)-2-hydroxypropyl]-N-(tricyclo[3.3.1.1$^{3,7}$]dec-1-ylmethyl)-benzamide, hydrochloride salt 2-Chloro-5-[(2R)-2-oxiranylmethyl]-N-(tricyclo[3.3.1.1$^{3,7}$]dec-1-ylmethyl)-benzamide (Example 5c) (452mg), ethylamine (70% aqueous solution, 5 mL) and tetrahydrofuiran (15 mL) were heated together at 50° C. under nitrogen for 20 hours, cooled and concentrated to give an oil. This was purified by Waters' MCX resin (mixed-mode cation exchanger) and then by column chromatography eluting with 19:1:0.1 dichloromethane/methanol/ammonia. The oil obtained was dissolved in dichloromethane (5 mL) and one molar (1M) ethereal hydrogen chloride (4 mL) was added. The mixture was concentrated to give the sub-titled compound as a solid (415 mg).

$^1$H NMR (400 MHz, d$_6$-DMSO) δ 8.29–8.26 (1H, t); 7.43–7.40 (1H, d); 7.30–7.28 (2H, m); 5.53–5.52 (1H, d); 3.98 (2H, br m); 2.94–2.82 (5H, m); 2.79–2.67 (3H, m); 1.94 (3H, br s); 1.69–1.58 (6H, br AB); 1.52 (6H, br s); 1.20–1.16 (3H, t).

MS: APCI(+ve) ion [M+H]$^+$ 405, 407 m.p. 218° C.

EXAMPLE 6

2-Chloro-5-[(2R)-2-hydroxy-3-[(1-methylethyl)amino]propyl]-N-(tricyclo[3.3.1.1$^{3,7}$]dec-1-ylmethyl)-benzamide, hydrochloride

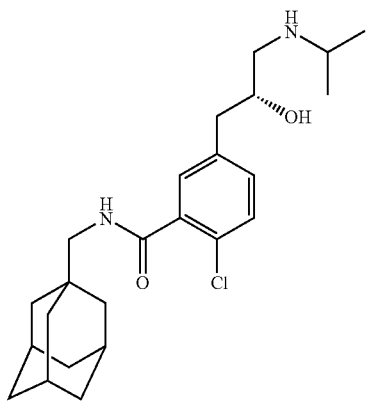

2-Chloro-5-[(2R)-2-oxiranylmethyl]-N-(tricyclo[3.3.1.1$^{3,7}$]dec-1-ylmethyl)-benzamide (Example 5c) (133 mg), isopropylamine (3 mL) and 1-methyl-2-pyrrolidinone (5 mL) were heated together at 80° C. in a sealed tube for 22 hours, cooled and poured into brine (50 mL), extracted into ethyl acetate (3×50 mL), washed with brine (3×50 mL), dried over anhydrous magnesium sulfate, filtered and concentrated to give an oil. This was purified by Waters' MCX resin and then by column chromatography eluting with 19:1:0.1 dichloromethane/methanol/ammonia. The oil obtained was dissolved in dichloromethane (5 mL) and 1M ethereal hydrogen chloride (4 mL) was added. The mixture was concentrated to give the titled compound as a solid (85 mg).

$^1$H NMR (400 MHz, d$_6$-DMSO) δ 8.29 (1H, br t); 7.43–7.41 (1H, d); 7.31–7.29 (2H, m); 5.52 (1H, br s); 3.99 (1H, br s); 2.98–2.92 (3H, m); 2.83–2.67 (3H, m); 1.94 (3H, br s); 1.69–1.59 (6H, br AB); 1.23–1.20 (6H, m).

MS: APCI(+ve) ion [M+H]$^+$ 419, 421 m.p. 189° C.

EXAMPLE 7

2-Chloro-5-[(2R)-2-hydroxy-3-[(3-hydroxypropyl)amino]propyl]-N-(tricyclo[3.3.1.1$^{3,7}$]dec-1-ylmethyl)-benzamide, hydrochloride salt

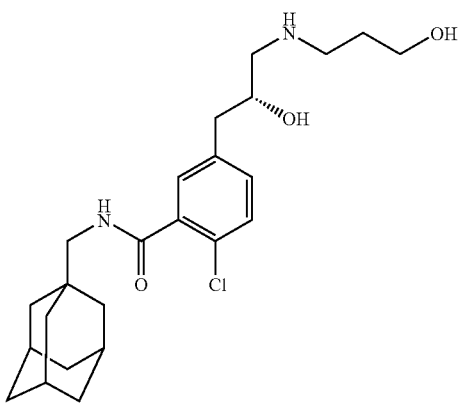

2-Chloro-5-[(2R)-2-oxiranylmethyl]-N-(tricyclo[3.3.1.1$^{3,7}$]dec-1-ylmethyl)-benzamide (Example 5c) (133 mg), 3-amino-1-propanol (3 mL) and 1-methyl-2-pyrrolidinone (5 mL) were heated together at 80° C. in a sealed tube for 22 hours, cooled and poured into brine (50 mL), extracted into ethyl acetate (3×50 mL), washed with brine (3×50 mL), dried over anhydrous magnesium sulfate, filtered and concentrated to give an oil. This was purified by Waters' MCX resin and then by column chromatography eluting with 9:1:0.1 dichloromethane/methanol/ammonia. This was further purified by reverse phase HPLC (gradient 25–95% acetonitrile in 0.2% aqueous trifluoroacetic acid on Xterra™ column). The oil obtained was dissolved in dichloromethane (5 mL) and 1M ethereal hydrogen chloride (4 mL) was added. The mixture was concentrated to give the titled compound as a solid (60 mg).

$^1$H NMR (400 MHz, d$_6$-DMSO) δ 8.28 (1H, br t); 7.42–7.40 (1H, d); 7.30–7.28 (2H, m); 5.53 (1H, br s); 4.78 (1H, br s); 4.00 (1H, br s); 3.50–3.45 (2H, br t); 3.00–2.92 (5H, m); 2.81–2.68 (3H, m); 1.94 (3H, br s); 1.76 (2H, br m); 1.69–1.58 (6H, br AB); 1.53 (6H, br s).

MS: APCI(+ve) ion [M+H]$^+$ 435, 437

M.p. 225° C.

EXAMPLE 8

2-Chloro-5-[(2R)-3-(dimethylamino)-2-hydroxypropyl]-N-(tricyclo[3.3.1.1$^{3,7}$]dec-1-ylmethyl)-benzamide, hydrochloride

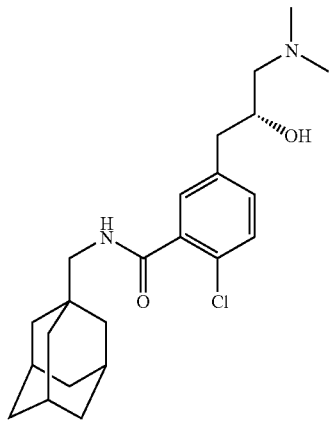

2-Chloro-5-[(2R)-2-oxiranylmethyl]-N-(tricyclo[3.3.1.1$^{3,7}$]dec-1-ylmethyl)-benzamide (Example 5c) (133 mg), dimethylamine (40% solution in water, 3 mL) and 1-methyl-2-pyrrolidinone (5 mL) were heated together at 80° C. in a sealed tube for 22 hours, cooled and poured into brine (50 mL), extracted into ethyl acetate (3×50 mL), washed with brine (3×50 mL), dried over anhydrous magnesium sulfate, filtered and concentrated to give an oil. This was purified by Waters' MCX resin and then by reverse phase HPLC (gradient 25–95% acetonitrile in 0.2% aqueous trifluoroacetic acid on Waters' Xterra™ column). The oil obtained was dissolved in dichloromethane (5 mL) and 1M ethereal hydrogen chloride (4 mL) was added. The mixture was concentrated to give the titled compound as a solid (41 mg).

$^1$H NMR (400 MHz, d$_6$-DMSO) δ 8.29–8.26 (1H, t); 7.43–7.41 (1H, d); 7.31–7.29 (2H, m); 5.64 (1H, br s); 4.11 (1H, br s); 3.15–2.98 (2H, m); 2.94–2.93 (2H, d); 2.79–2.66 (7H, m); 1.94 (3H, br s); 1.69–1.58 (6H, br AB); 1.53 (6H, br s).

MS: APCI(+ve) ion [M+H]$^+$ 405, 407 m.p. 198° C.

EXAMPLE 9

2-Chloro-5-[(1S)-1-hydroxy-2-(methylamino)ethyl]-N-(tricyclo[3.3.1.1$^{3,7}$]dec-1-ylmethyl)benzamide hydrochloride

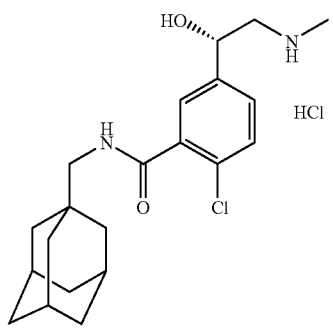

a) 2-Chloro-5-ethenyl-N-(tricyclo[3.3.1.1$^{3,7}$]dec-1-ylmethyl)benzamide

A solution of 5-bromo-2-chloro-N-(tricyclo[3.3.1.1$^{3,7}$]dec-1-ylmethyl)benzamide (prepared as described in WO 00/61569) (1.0 g), tetrakis(triphenylphosphine)palladium(0) (96 mg) and tributylvinyltin (1.15 mL) in toluene (15 mL) was heated at reflux for 3 hours, then cooled to room temperature, diluted with acetone (30 mL) and treated with cesium fluoride (10% aq, 10 mL) at room temperature for 2 hours. The resulting mixture was filtered through celite with further washing with toluene and concentrated. Water was added and the mixture was extracted with ethyl acetate. The combined organic phases were washed with water, dried over anhydrous magnesium sulfate and concentrated. The resulting oil was purified by column chromatography (ethyl acetate:isohexane 100:1 to 80:20) to give the sub-titled compound as a white solid (0.87 g).

$^1$H NMR (400 MHz, CDCl$_3$) δ 7.25 (d, 1H), 7.39 (dd, 1H), 7.35 (d, 1H), 6.68 (dd, 1H), 6.25 (s, 1H), 5.78 (d, 1H), 3.33 (d, 1H), 3.17 (d, 2H), 2.01 (s, 3H), 1.73 (d, 3H), 1.65 (d, 3H), 1.60 (s, 6H).

b) 2-Chloro-5-[(1S)-1-hydroxy-2-(methylamino)ethyl]-N-(tricyclo[3.3.1.1$^{3,7}$]dec-1-ylmethyl)benzamide hydrochloride m-Chloroperoxybenzoic acid (mCPBA) (50%, 0.44 g) was added portionwise over 10 minutes to a solution of 2-chloro-5-ethenyl-N-(tricyclo[3.3.1.1$^{3,7}$]dec-1-ylmethyl)benzamide (Example 9a)) (0.42 g), (S,S)-[N,N'-bis(3,5-di-tertbutylsalicylidene)-1,2-cyclohexanediaminato(2-)]manganese(III) chloride (44 mg) and N-methylmorpholine (0.74 g) in dichloromethane (10 mL) at −78° C. After stirring for 8 hours, a further portion of mCPBA (0.13 g) was added and the solution was left to warm slowly to room temperature over 16 hours. Sodium hydroxide (NaOH) (2M) was added, stirred for 1 hour and then methylamine (2M in methanol, 2 mL) was added. After stirring for 24 hours the reaction was concentrated, dichloromethane and water were added, the phases were separated and the aqueous was extracted with dichloromethane. The combined organic phases were dried over anhydrous sodium sulfate and concentrated. The resulting oil was purified by reverse phase HPLC (gradient 25–95% methanol in 1% aqueous trifluoroacetic acid). Further purification was performed by column chromatography (methanol/dichloromethane/ammonia (0.88) 1:20:0.5 to 15:100:0.5) gave an oil. Addition of excess 1M ethereal hydrogen chloride gave the titled compound as a white solid (158mg).

$^1$H NMR (400 MHz, d$_6$-DMSO) δ 8.33 (t, 1H), 8.20 (s, 1H), 7.48 (d, 1H), 7.45 (dd, 1H), 7.40 (d, 1H), 6.20 (s, 1H), 4.91 (d, 1H), 3.25–3.40 (m, 1H), 3.08 (dd, 1H), 2.95 (d, 2H), 2.85–2.95 (m, 1H), 2.55 (s, 3H), 1.95 (s, 3H), 1.63 (dd, 6H), 1.52 (s, 6H).

EXAMPLE 10

2-Chloro-5-[(1R)-1-hydroxy-2-(methylamino)ethyl]-N-(tricyclo[3.3.1.1³,⁷]dec-1-ylmethyl)benzamide, hydrochloride

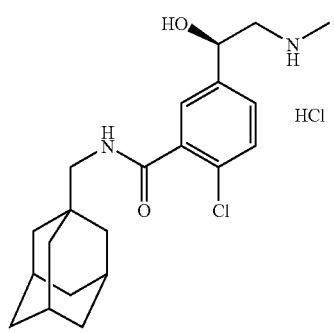

The titled compound was prepared by the method of Example 9b) using (R,R)-[N,N'-bis (3,5-di-tertbutylsalicylidene)-1,2-cyclohexanediaminato(2-)]manganese(III) chloride.

¹H NMR (400 MHz, d₆-DMSO) δ 8.55 (t, 1H), 8.34 (s, 1H), 7.49 (d, 1H), 7.44 (dd, 1H), 7.40 (d, 1H), 6.26 (s, 1H), 4.93 (d, 1H), 3.26–3.40 (m, 1H), 3.11 (dd, 1H), 2.95 (d, 2H), 2.95 (dd, 1H), 2.57 (s, 3H), 1.94 (s, 3H), 1.64 (dd, 6H), 1.52 (s, 6H).

EXAMPLE 11

2-Chloro-5-[(1R)-2-(ethylamino)-1-hydroxyethyl]-N-(tricyclo[3.3.1.1³,⁷]dec-1-ylmethyl)benzamide

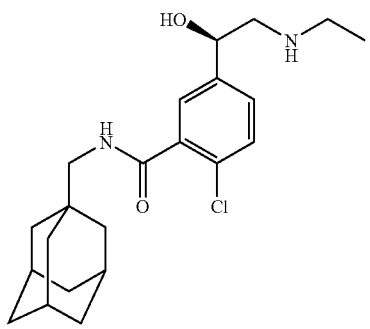

The titled compound was prepared by the method of Example 9b) using (R,R)-[N,N'-bis (3,5-di-tertbutylsalicylidene)-1,2-cyclohexanediaminato(2-)]manganese(III) chloride and ethylamine.

¹H NMR (400 MHz, d₆-DMSO) δ 8.30 (1H, t), 7.43–7.32 (3H, m), 5.40 (1H, s), 4.64 (1H, dd), 2.93 (2H, d), 2.68–2.50 (4H, m), 1.94 (3H, s), 1.63 (6H, dd), 1.52 (6H, d), 1.00 (3H, t).

EXAMPLE 12

2-Chloro-5-[(1R)-1-hydroxy-2-[(3-hydroxypropyl)amino]ethyl]-N-(tricyclo [3.3.1.1³,⁷]dec-1-ylmethyl)benzamide

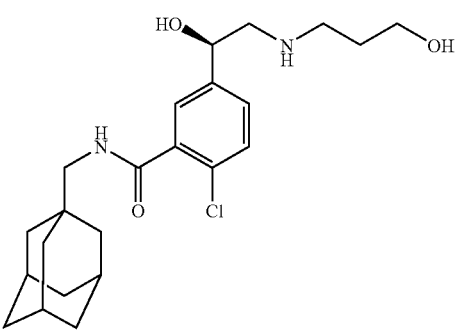

The titled compound was prepared by the method of Example 9b) using (R,R)-[N,N'-bis (3,5-di-tertbutylsalicylidene)-1,2-cyclohexanediaminato(2-)]manganese(III) chloride and 3-aminopropan-1-ol.

¹H NMR (400 MHz, d₆-DMSO) δ 7.43–7.32 (3H, m), 5.40 (1H, s), 4.63 (1H, s), 3.44 (2H, t), 2.93 (2H, d), 2.66–2.55 (4H, m), 1.94 (3H, s), 1.64 (6H, q), 1.57–1.50 (2H, m), 1.53 (6H, s).

EXAMPLE 13

2-Chloro-5-[(2S)-2-hydroxy-3-(methylamino)propyl]-N-(tricyclo[3.3.1.1³,⁷]dec-1-ylmethyl)-benzamide, hydrochloride

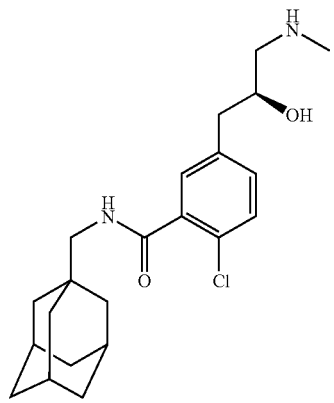

a) 2-Chloro-5-(2,3-dihydroxypropyl)-N-(tricyclo[3.3.1.1³,⁷]dec-1-ylmethyl)-benzamide 2-Chloro-5-(2-propenyl)-N-(tricyclo[3.3.1.1³,⁷]dec-1-ylmethyl)-benzamide (prepared as described in Example 5a) (1.99 g), tert-butanol (40 mL) and water (40 mL) were stirred together under nitrogen and AD-mix-α was added. The mixture was then stirred at room temperature for 20 hours. Sodium sulfite (2 g) was added and the mixture was stirred for 10 minutes. Water (100 mL) and ethyl acetate (100 mL) were then added. The layers were separated and the aqueous layer was further extracted with ethyl acetate (2×100 mL). The combined extracts were dried over anhydrous magnesium sulfate, filtered and concentrated to give the crude product. Purification was performed by column chromatography eluting with 5:95 methanol/ethyl acetate to give the sub-titled compound as a solid (1.77 g).

$^1$H NMR (400 MHz, CDCl$_3$) δ 7.59 (1H, d); 7.36–7.34 (1H, d); 7.26–7.23 (1H, dd); 6.29 (1H, br t); 3.98–3.91 (1H, m); 3.72–3.67 (1H, m); 3.54–3.48 (1H, m); 3.18–3.17 (2H, d); 2.83–2.73 (2H, m); 2.25–2.24 (1H, d); 2.01 (3H, br s); 1.98–1.95 (1H, t); 1.75–1.64 (6H, br AB); 1.59 (6H, br s).

MS (ES+) ion [M+H]$^+$ 378, 380 b) 2-Chloro-5-[(2S)-2-oxiranylmethyl]-N-(tricyclo[3.3.1.1$^{3,7}$]dec-1-ylmethyl)-benzamide 2-Chloro-5-(2,3-dihydroxypropyl)-N-(tricyclo[3.3.1.1$^{3,7}$]dec-1-ylmethyl)-benzamide (Example 13a) (1.77 g), triethylamine (0.7 mL), dichloromethane (160 mL) and tetrahydrofuran (40 mL) were cooled to 5° C. under nitrogen and methanesulfonyl chloride (0.35 mL) was added. The mixture was then stirred at 5° C. for 15 minutes, poured into aqueous sodium bicarbonate solution (75 mL), extracted into dichloromethane (3×100 mL), dried over anhydrous magnesium sulfate, filtered and concentrated to give the crude product. This was purified by column chromatography eluting with ethyl acetate to give the mesylate (1.06 g). The mesylate (971 mg) in methanol (45 mL) was stirred under nitrogen and potassium carbonate (592 mg) was added. The mixture was then stirred at room temperature for 1 hour, poured into water (50 mL), extracted into ethylacetate (3×50 mL), dried over anhydrous magnesium sulfate, filtered and concentrated to give the crude product. This was purified by column chromatography eluting with 2:1 iso-hexane/ethylacetate to give the epoxide (595 mg). (1S, 2S)-(–)-N,N'-Bis(3,5-di-t-butylsalicydene)-1,2-cyclohexanediaminocobalt(II) (0.20 g), acetic acid (0.1 mL) and toluene (2 mL) were stirred together in air for 1.5 hours. The solvents were then removed in vacuo and the resultant brown glass was dried under high vacuum for 2 hours. The epoxide described above (595 mg), water (1 mL) and tetrahydrofuran (30 mL) were then added to this and the mixture stirred under nitrogen for 92 hours, concentrated and purified by column chromatography eluting with 2:1 isohexane/ethyl acetate to give the sub-titled compound (0.219 g).

MS (ES+) ion [M+H]$^+$ 360, 362 c) 2-Chloro-5-[(2S)-2-hydroxy-3-(methylamino)propyl]-N-(tricyclo[3.3.1.1$^{3,7}$]dec-1-ylmethyl)-benzamide, hydrochloride salt 2-Chloro-5-[(2S)-2-oxiranylmethyl]-N-(tricyclo[3.3.1.1$^{3,7}$]dec-1-ylmethyl)-benzamide (Example 13b) (110 mg), methylamine (40% aqueous solution, 2 mL) and tetrahydrofuran (10 mL) were heated together at 50° C. under nitrogen for 20 hours, cooled and concentrated to give an oil. This was purified by Waters' MCX resin and then by column chromatography eluting with 9:1:0.1 dichloromethane/methanol/ammonia. The oil obtained was dissolved in dichloromethane (5 mL) and 1M ethereal hydrogen chloride (4 mL) was added. The resulting white solid was filtered off to give the titled compound (121 mg).

$^1$H NMR (400 MHz, d$_6$-DMSO) δ 8.29–8.26 (1H, t); 7.43–7.40 (1H, d); 7.30–7.27 (2H, m); 5.55–5.53 (1H, d); 3.97 (1H, br m); 2.97–2.90 (3H, m); 2.80–2.67 (3H, m); 2.53 (3H, s); 1.94 (3H, br s); 1.69–1.58 (6H, br AB); 1.52 (6H, br s).

MS APCI(+ve) ion [M+H]$^+$ 391, 393 m.p. 196° C.

EXAMPLE 14

2-Chloro-5-[(2S)-3-(ethylamino)-2-hydroxypropyl]-N-(tricyclo [3.3.1.1$^{3,7}$]dec-1-ylmethyl)-benzamide, hydrochloride salt

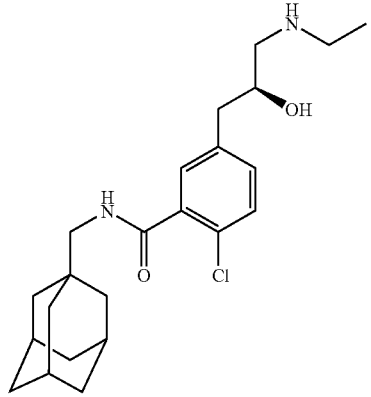

2-Chloro-5-[(2S)-2-oxiranylmethyl]-N-(tricyclo[3.3.1.1$^{3,7}$]dec-1-ylmethyl)-benzamide (Example 13b) (110 mg), ethylamine (70% aqueous solution, 2 mL) and tetrahydrofuran (10 mL) were heated together at 50° C. under nitrogen for 20 hours, cooled and concentrated to give an oil. This was purified by Waters' MCX resin and then by column chromatography eluting with 9:1:0.1 dichloromethane/methanol/ammonia. The oil obtained was dissolved in dichloromethane (5 mL) and 1M ethereal hydrogen chloride (4 mL) was added. The resulting white solid was filtered off to give the titled compound (109 mg).

$^1$H NMR (400 MHz, d$_6$-DMSO) δ 8.30–8.27 (1H, t); 7.43–7.40 (1H, d); 7.30–7.28 (2H, m); 5.54–5.53 (1H, d); 3.99 (1H, br m); 3.00–2.87 (5H, m); 2.82–2.67 (3H, m); 1.94 (3H, br s); 1.69–1.58 (6H, br AB); 1.52 (6H, br s); 1.20–1.16 (3H, t).

MS APCI(+ve) ion [M+H]$^+$ 405, 407 m.p. 214° C.

EXAMPLE 15

2-Chloro-5-[(2R)-2-hydroxy-3-(methylamino)propyl]-N-(tricyclo[3.3.1.1$^{3,7}$]dec-1-ylmethyl)benzamide, benzoic acid salt

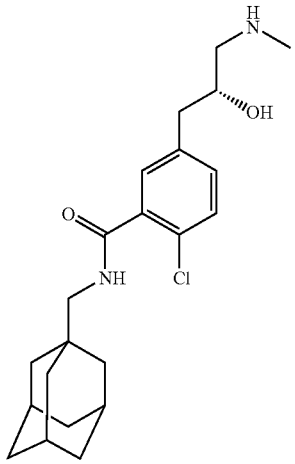

a) 2-Chloro-5-iodo-N-[(4-methoxyphenyl)methyl]-N-(tricyclo[3.3.1.1³,⁷]dec-1-ylmethyl)benzamide Potassium t-butoxide (18.8 g) was added to a stirred solution of 2-chloro-5-iodo-N-(tricyclo [3.3.1.1³,⁷]dec-1-ylmethyl)benzamide (prepared as described in WO 99/29661) (60.0 g) in anhydrous tetrahydrofuran (600 mL) at 20° C. under nitrogen. After the addition was complete, 4-methoxybenzyl chloride (20.8 mL) was added. The mixture was heated to reflux for 12 hours and then cooled to room temperature. Water (600 mL) was added and the mixture extracted with dichloromethane (1.2 L then 400 mL). Organic extracts were dried over anhydrous magnesium sulphate, filtered and evaporated under reduced pressure.

The residual solid was suspended in iso-hexane/t-butyl methyl ether (9:1, 1 L), stirred at reflux for 1 hour and then cooled to room temperature. The solid was filtered then dried in vacuo to give the sub-titled compound (72.88 g).

$^1$H NMR (400 MHz, CDCl$_3$) (major rotamer only) δ 1.62–1.77 (2H, m), 2.01 (3H, s), 2.73 (1H, d), 3.71 (1H, d), 3.80 (3H, s), 4.38 (2H, ABq), 6.83 (2H, d), 6.92 (2H, d), 7.10 (1H, d), 7.42 (1H, d), 7.55 (1H, dd).

MS (APCI) ion [M+H]$^+$ 550/552 b) 2-Chloro-5-[(2S)-3-chloro-2-hydroxypropyl]-N-[(4-methoxyphenyl)methyl]-N-(tricyclo[3.3.1.1³,⁷]dec-1-ylmethyl)benzamide iso-Propylmagnesium chloride solution (2M in tetrahydrofuran, 72.9 mL) was added to a stirred solution of 2-chloro-5-iodo-N-[(4-methoxyphenyl)methyl]-N-(tricyclo [3.3.1.1³,⁷]dec-1-ylmethyl)benzamide (Example 15a) (72.87 g) in anhydrous tetrahydrofuran (1 L) at 0° C. under nitrogen. After 30 minutes, copper(I) bromide dimethylsulphide complex (0.68 g) followed by (R)-(−)epichlorohydrin (11.4 mL) were added. The mixture was warmed to 30° C. for 2 hours then diluted with saturated sodium bicarbonate solution (1 L) and water (500 mL) then extracted with ethyl acetate (2×1 L). Organic extracts were dried over anhydrous magnesium sulphate, filtered and evaporated under reduced pressure. The residual oil was dissolved in methanol (600 mL), stirred overnight and the precipitated solid filtered and dried in vacuo to give the titled compound (52.25 g).

$^1$H NMR (400 MHz, CDCl$_3$) (major rotamer only) δ 1.50–1.78 (2H, m), 2.01 (3H, s), 2.63 (1H, dd), 2.68–2.84 (2H, m), 3.24–3.30 (1H, m), 3.40 (1H, dt), 3.76–3.88 (5H, m), 4.40 (2H, ABq), 6.82 (2H, d), 6.95 (2H, d), 7.05 (1H, d), 7.12 (1H, dd), 7.31 (1H, d).

MS (APCI) ion [M+H]$^+$ 516/518/520 c) 2-Chloro-5-[(2R)-2-hydroxy-3-(methylamino)propyl]-N-(tricyclo[3.3.1.1³,⁷]dec-1-ylmethyl)benzamide A solution of 2-chloro-5-[(2S)-3-chloro-2-hydroxypropyl]-N-[(4-methoxyphenyl)methyl]-N-(tricyclo [3.3.1.1³,⁷]dec-1-ylmethyl)benzamide (Example 15b)) (52.24 g, 101 mmol) in trifluoroacetic acid (260 mL) was heated at 50° C. for 16 hours then evaporated to a viscous oil. The oil was redissolved in methanol (500 mL) and evaporated in vacuo. The residual solid was dissolved in tetrahydrofuran (300 mL) and a solution of sodium hydroxide (8.08 g) in methanol (100 mL) was added. After 15 minutes, 40 wt % aqueous methylamine solution (520 mL) was added. After 2 hours, the solution was decanted from a brown oil and evaporated under reduced pressure at 50° C. The resulting suspension was diluted with water (2 L), acidified to pH<2 with 37 wt % hydrochloric acid, and extracted with ethyl acetate (1 L). The organic layer was back-extracted with 0.5M hydrochloric acid (1 L). Combined aqueous extracts were adjusted to pH 11–12 with 50 wt % sodium hydroxide solution, and extracted with ethyl acetate (2×1 L). Organic extracts were dried over anhydrous magnesium sulphate, filtered and evaporated under reduced pressure to give the titled compound as a white solid (34.52 g).

$^1$H NMR (400 MHz, CDCl$_3$) δ 1.59 (6H, s), 1.65 (3H, d), 1.73 (3H, d), 2.01 (3H, s), 2.42 (3H, s), 2.49 (1H, t), 2.68 (1H, dd), 2.71 (2H, d), 3.17 (2H, d), 3.80–3.87 (1H, m), 6.29 (1H, s), 7.25 (1H, d), 7.33 (1H, d), 7.58 (1H, s).

MS (APCI) ion [M+H]$^+$ 510, 512 d) 2-Chloro-5-[(2R)-2-hydroxy-3-(methylamino)propyl]-N-(tricyclo[3.3.1.1³,⁷]dec-1-ylmethyl)benzamide benzoic acid salt Benzoic acid (11.07 g) was added to a suspension of 2-chloro-5-[(2R)-2-hydroxy-3-(methylamino)propyl]-N-(tricyclo[3.3.1.1³,⁷]dec-1-ylmethyl)benzamide (Example 15c)) (33.54 g, 86 mmol) in 2-propanol (333 mL) and the mixture heated to reflux whereupon a clear solution was obtained. t-Butyl methyl ether (1 L) was added dropwise over 30 minutes and the solution maintained at reflux. The solution was allowed to cool to room temperature, stirred for a further 2 hours and solid collected by filtration, washed with t-butyl methyl ether and dried in vacuo at 40° C. to give the titled compound (24.5 g). The mother liquors were evaporated in vacuo and the residue dissolved in 2-propanol (50 mL) at reflux, t-butyl methyl ether (150 mL) was added and a second crop was isolated as before to give further titled compound (13 g).

$^1$H NMR (400 MHz, d$_6$-DMSO) δ 1.52 (6H, s), 1.59 (3H, d), 1.67 (3H, d), 1.94 (3H, s), 2.43 (3H, s), 2.60–2.68 (2H, m), 2.72–2.79 (2H, m), 2.93 (2H, d), 3.88–3.93 (1H, m), 7.26 (1H, s), 7.27 (1H, d), 7.35–7.40 (3H, m), 7.47 (1H, t), 7.90 (2H, d), 8.29 (1H, t).

MS (APCI) ion [M+H]$^+$ 391, 393

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 µl of test solution comprising 200 µl of a suspension of THP-1 cells (2.5×10$^6$ cells/ml) containing 10$^{-4}$M ethidium bromide, 25 µl of a high potassium buffer solution containing 10$^{-5}$M bbATP, and 25 µl of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of the Examples demonstrated antagonist activity, having a pIC$_{50}$ figure>4.50. For example, the compounds of Examples 1, 8 and 10 had pIC$_{50}$ values of 8.0, 8.4 and 8.2 respectively.

The invention claimed is:

1. A compound of formula wherein m represents 1, 2 or 3;
each R$^1$ independently represents a hydrogen or halogen atom;
one of R$^2$ and R$^3$ represents halogen, nitro, amino, hydroxyl, or a group selected from (i) C$_1$–C$_6$ alkyl optionally substituted by at least one halogen atom, (ii) C$_3$–C$_8$ cycloalkyl, (iii) C$_1$–C$_6$ alkoxy optionally substituted by at least one halogen atom, and (iv) C$_3$–C$_8$ cycloalkyloxy, and the other of R$^2$ and R$^3$ represents a hydrogen or halogen atom;
n represents 0, 1 or 2; and
R$^4$ and R$^5$ each independently represent a hydrogen atom or a C$_1$–C$_6$ alkyl group optionally substituted by at least one substituent selected from hydroxyl, halogen and C$_1$–C$_6$ alkoxy;
or a pharmaceutically acceptable salt or solvate thereof.

2. A compound according to claim 1, wherein m is 1.

3. A compound according to claim 1, wherein R$^3$ represents a hydrogen atom.

4. A compound according to claim 1, wherein n is 1.

5. A compound according to claim 4, which has the following stereochemistry:

6. A compound according to claim 1, wherein R$^4$ and R$^5$ each independently represent a hydrogen atom or a C$_1$–C$_6$ alkyl group optionally substituted by at least one hydroxyl group.

7. A compound according to claim 1, wherein
m represents 1;
each R$^1$ represents a hydrogen atom;
one of R$^2$ and R$^3$ represents a halogen atom, and the other of R$^2$ and R$^3$ represents a hydrogen atom;
n is 0, 1 or 2; and
R$^4$ and R$^5$ each independently represent a hydrogen atom or a group selected from —CH$_3$, —C$_2$H$_5$, —CH(CH$_3$)$_2$ and —(CH$_2$)$_3$OH.

8. A compound according to claim 1, wherein
m represents 1;
each R$^1$ represents a hydrogen atom;
one of R$^2$ and R$^3$ represents a halogen atom, and the other of R$^2$ and R$^3$ represents a hydrogen atom;
n is 0, 1 or 2; and
one of R$^4$ and R$^5$ represents a hydrogen atom or —CH$_3$ and the other of R$^4$ and R$^5$ represents a group selected from —CH$_3$, —C$_2$H$_5$, —CH(CH$_3$)$_2$ and —(CH$_2$)$_3$OH.

9. A compound being selected from any one of:
2-Chloro-5-[(3S)-3-hydroxy-4-(methylamino)butyl]-N-(tricyclo[3.3.1.1$^{3,7}$]dec-1-ylmethyl)benzamide,
2-Chloro-5-[(3S)-3-hydroxy-4-(ethylamino)butyl]-N-(tricyclo[3.3.1.1$^{3,7}$]dec-1-ylmethyl)benzamide,
2-Chloro-5-[(3S)-3-hydroxy-4-(1-methylethylamino)butyl]-N-(tricyclo [3.3.1.1$^{3,7}$]dec-1-ylmethyl)benzamide,
2-Chloro-5-[(3R)-3-hydroxy-4-(methylamino)butyl]-N-(tricyclo[3.3.1.1$^{3,7}$]dec-1-ylmethyl)benzamide,
2-Chloro-5-[(2R)-3-(ethylamino)-2-hydroxypropyl]-N-(tricyclo[3.3.1.1$^{3,7}$]dec-1-ylmethyl)-benzamide hydrochloride,
2-Chloro-5-[(2R)-3-(ethylamino)-2-hydroxypropyl]-N-(tricyclo[3.3.1.1$^{3,7}$]dec-1-ylmethyl)-benzamide,
2-Chloro-5-[(2R)-2-hydroxy-3-[(1-methylethyl)amino]propyl]-N-(tricyclo[3.3.1.1$^{3,7}$]dec-1-ylmethyl)-benzamide hydrochloride,
2-Chloro-5-[(2R)-2-hydroxy-3-[(1-methylethyl)amino]propyl]-N-(tricyclo[3.3.1.1$^{3,7}$]dec-1-ylmethyl)-benzamide,
2-Chloro-5-[(2R)-2-hydroxy-3-[(3-hydroxypropyl)amino]propyl]-N-(tricyclo[3.3.1.1$^{3,7}$]dec-1-ylmethyl)-benzamide hydrochloride,
2-Chloro-5-[(2R)-2-hydroxy-3-[(3-hydroxypropyl)amino]propyl]-N-(tricyclo[3.3.1.1$^{3,7}$]dec-1-ylmethyl)-benzamide,
2-Chloro-5-[(2R)-3-(dimethylamino)-2-hydroxypropyl]-N-(tricyclo[3.3.1.1$^{3,7}$]dec-1-ylmethyl)-benzamide hydrochloride,
2-Chloro-5-[(2R)-3-(dimethylamino)-2-hydroxypropyl]-N-(tricyclo[3.3.1.1$^{3,7}$]dec-1-ylmethyl)-benzamide,
2-Chloro-5-[(1S)-1-hydroxy-2-(methylamino)ethyl]-N-(tricyclo[3.3.1.1$^{3,7}$]dec-1-ylmethyl)benzamide hydrochloride,
2-Chloro-5-[(1S)-1-hydroxy-2-(methylamino)ethyl]-N-(tricyclo[3.3.1.1$^{3,7}$]dec-1-ylmethyl)benzamide,
2-Chloro-5-[(1R)-1-hydroxy-2-(methylamino)ethyl]-N-(tricyclo[3.3.1.1$^{3,7}$]dec-1-ylmethyl)benzamide hydrochloride,
2-Chloro-5-[(1R)-1-hydroxy-2-(methylamino)ethyl]-N-(tricyclo[3.3.1.1$^{3,7}$]dec-1-ylmethyl)benzamide,
2-Chloro-5-[(1R)-2-(ethylamino)-1-hydroxyethyl]-N-(tricyclo[3.3.1.1$^{3,7}$]dec-1-ylmethyl)benzamide, 2-Chloro-5-[(1R)-1-hydroxy-2-[(3-hydroxypropyl)amino]ethyl]-N-(tricyclo[3.3.1.1³,⁷]dec-1-ylmethyl)benzamide, 2-Chloro-5-[(2S)-2-hydroxy-3-(methylamino)propyl]-N-(tricyclo[3.3.1.1³,⁷]dec-1-ylmethyl)-benzamide hydrochloride, 2-Chloro-5-[(2S)-2-hydroxy-3-(methylamino)propyl]-N-(tricyclo[3.3.1.1³,⁷]dec-1-ylmethyl)-benzamide, 2-Chloro-5-[(2S)-3-(ethylamino)-2-hydroxypropyl]-N-(tricyclo[3.3.1.1³,⁷]dec-1-ylmethyl)-benzamide hydrochloride, 2-Chloro-5-[(2S)-3-(ethylamino)-2-hydroxypropyl]-N-(tricyclo[3.3.1.1³,⁷]dec-1-ylmethyl)-benzamide, 2-Chloro-5-[(2R)-2-hydroxy-3-(methylamino)propyl]-N-(tricyclo[3.3.1.1³,⁷]dec-1-ylmethyl)benzamide benzoic acid salt, 2-Chloro-5-[(2R)-2-hydroxy-3-(methylamino)propyl]-N-(tricyclo[3.3.1.1³,⁷]dec-1-ylmethyl)benzamide, and all pharmaceutically acceptable salts and solvates thereof.

10. A process for the preparation of a compound according to claim 1, which comprises:

(i) when n is 0, reacting a compound of formula

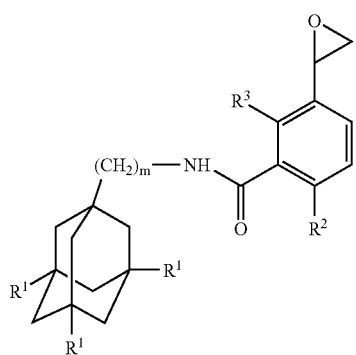

(II)

wherein m, $R^1$, $R^2$ and $R^3$ are as defined in formula (I), with a compound of formula (III), $HNR^4R^5$, wherein $R^4$ and $R^5$ are as defined in formula (I); or (ii) when n is 1, reacting a compound of formula

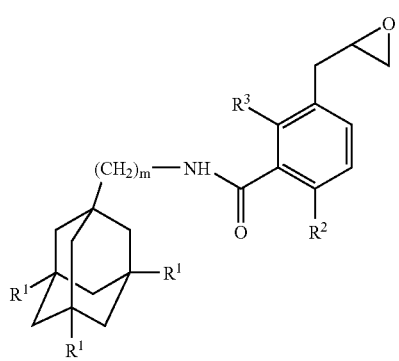

(IV)

wherein m, $R^1$, $R^2$ and $R^3$ are as defined in formula (I), with a compound of formula (III) as defined in (i) above; or (iii) when n is 2, reacting a compound of formula

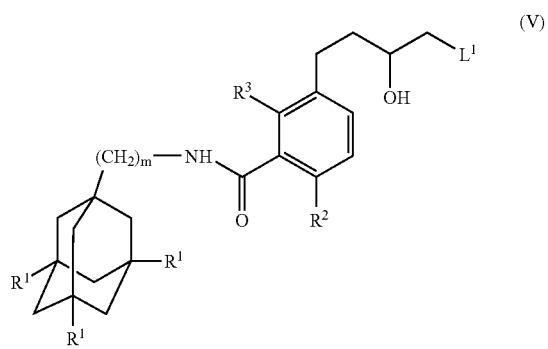

(V)

wherein $L^1$ is a leaving group and m, $R^1$, $R^2$ and $R^3$ are as defined in formula (I), with a compound of formula (III) as defined in (i) above; or (iv) when n is 1, reacting a compound of formula

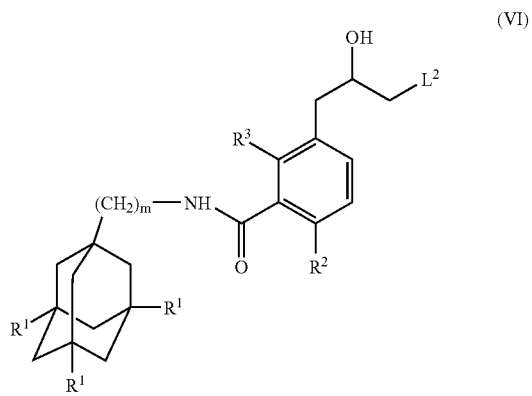

(VI)

wherein $L^2$ is a leaving group and m, $R^1$, $R^2$ and $R^3$ are as defined in formula (I), with a compound of formula (III) as defined in (i) above;

and optionally after (i), (ii) (iii) or (iv) carrying out one or more of the following:

converting the compound obtained to a further compound of formula (I)

forming a pharmaceutically acceptable salt or solvate of the compound.

11. A pharmaceutical composition comprising a compound of formula (I) or a pharmaceutically acceptable salt or solvate thereof as claimed in claim 1 in association with a pharmaceutically acceptable adjuvant, diluent or carrier.

12. A process for the preparation of a pharmaceutical composition which comprises mixing a compound of formula (I) or a pharmaceutically acceptable salt or solvate thereof as defined in claim 1 with a pharmaceutically acceptable adjuvant, diluent or carrier.

13. A method of treating rheumatoid arthritis or osteoarthritis which comprises administering to a patient a therapeutically effective amount of a compound of formula (I) or a pharmaceutically acceptable salt or solvate thereof as claimed in claim 1.

14. A method of treating an obstructive airways disease which comprises administering to a patient a therapeutically effective amount of a compound of formula (I) or a pharmaceutically acceptable salt or solvate thereof as claimed in claim 1.

15. The method of claim 14, wherein the obstructive airways disease is asthma or chronic obstructive pulmonary disease.

16. A method of treating atherosclerosis which comprises administering to a patient a therapeutically effective amount of a compound of formula (I) or a pharmaceutically acceptable salt or solvate thereof as claimed in claim 1.

* * * * *